US009546372B2

(12) United States Patent
Champagne et al.

(10) Patent No.: US 9,546,372 B2
(45) Date of Patent: Jan. 17, 2017

(54) REGULATORY ELEMENTS AND USES THEREOF

(71) Applicant: SYNTHETIC GENOMICS, INC., La Jolla, CA (US)

(72) Inventors: Michele M. Champagne, San Diego, CA (US); Toby H. Richardson, San Diego, CA (US); Jun Urano, Irvine, CA (US)

(73) Assignee: Synthetic Genomics, Inc., La Jolla, CA (US)

( * ) Notice: Subject to any disclaimer, the term of this patent is extended or adjusted under 35 U.S.C. 154(b) by 448 days.

(21) Appl. No.: 13/915,522

(22) Filed: Jun. 11, 2013

(65) Prior Publication Data
US 2014/0363892 A1    Dec. 11, 2014

(51) Int. Cl.
*C12N 15/82* (2006.01)
*C12N 15/79* (2006.01)

(52) U.S. Cl.
CPC ........... *C12N 15/8216* (2013.01); *C12N 15/79* (2013.01)

(58) Field of Classification Search
CPC ..... C12N 15/8216; C12N 15/79; C12N 18/85; C12N 15/82
See application file for complete search history.

(56) References Cited

U.S. PATENT DOCUMENTS

| | | | |
|---|---|---|---|
| 7,083,967 B1 * | 8/2006 | Kakefuda et al. | 435/232 |
| 7,449,568 B2 | 11/2008 | Fukuda et al. | |
| 7,790,958 B2 | 9/2010 | Boukharov et al. | |
| 7,816,510 B2 * | 10/2010 | Wu et al. | 536/24.1 |
| 8,119,859 B2 | 2/2012 | Vick et al. | |
| 8,314,228 B2 | 11/2012 | Kilian et al. | |
| 8,709,765 B2 | 4/2014 | Bailey et al. | |
| 8,865,468 B2 | 10/2014 | Kilian et al. | |
| 2006/0272045 A1 | 11/2006 | Hinkle et al. | |
| 2009/0317904 A1 | 12/2009 | Vick et al. | |
| 2011/0107468 A1 | 5/2011 | Flasinski et al. | |
| 2011/0300633 A1 | 12/2011 | Adachi et al. | |
| 2013/0102040 A1 | 4/2013 | Radakovits et al. | |

FOREIGN PATENT DOCUMENTS

WO    WO 00/04196 A2    1/2000

OTHER PUBLICATIONS

Evertsz et al, (Biotechniques 31(5): 1182-1192, 2001).*
Jinkerson et al.: "*Genomic insights from the oleaginous model alga Nannochloropsis gaditana*"; Bioengineered, Jan. 1, 2013, vol. 4, No. 1, pp. 37-43.
Carpinelli et al.: "*Chromosome Scale Genome Assembly and Transcriptome Profiling of Nannochloropsis gaditana in Nitrogen Depletion*"; Mol Plant, Sep. 24, 2013; Entire document and supplemental file.
*Nannochibropsis gaditana*: -999 by from NG_chr17:256,679 . . . 255,680, Sep. 24, 2013 [online]. [Retrieved on Jan. 12, 2014]. Retrieved from the Internet: <URL: http://genomes.cribi.unipclit/gb2/gbrowse/public/nannochloropsis_gaditana/?name=NG_c > cited as supplement to Carpinelli.
Wei et al.: "*Nannochloropsis plastid and mitochondrial phylogenomes reveal organelle diversification mechanism and intragenus phylotyping strategy in microalgae*" BMC Genomics 2013;14:534; Aug. 5, 2013, 17 pages.
International Search Report regarding PCT/US2013/045263.
Abeel et al.: "*Generic eukaryotic core promoter prediction using structural features of DNA*"; Genome Research, 2008, vol. 18, pp. 310-323.
Chen et al.: *Conditional Production of a Functional Fish Growth Hormone in the Transgenic Line of Nannochloropsis Oculata (Eustigmatophyceae)*; J. Phycol, 2008, vol. 44, pp. 768-776.
Chipman et al.: "*Biosynthesis of 2-aceto-2-hydroxy acids : acetolactate synthases and acetohydroxyacid synthases*"; Biochimica et Biophysica Acta 1385 (1998) pp. 401-419.
Dikstein, Rivka: "*The unexpected traits associated with core promoter elements*"; Landes Bioscience Transcription, 2011, 2:5, pp. 201-206.
Ferrante et al.: "A n Optimized, Chemically Regulated Gene Expression System for *Chlamydomonas*"; PLoS ONE, Sep. 2008, vol. 3, Issue 9, e3200, 10 pages.
Gerrish et al.: "*Pancreatic β Cell-specific Transcription of the pdx-1 Gene*"; J. Bio Chem, Feb. 4, 2000, vol. 275, No. 5, pp. 3485-3492.
Hallmann et al.: "*Swapped green algal promoters: aphVIII-based gene constructs with Chlamydomonas flanking sequences work as dominant selectable markers in Volvox and vice versa*"; Plant Cell Rep, (2006) 25: 582-591.
Heintzman et al.: "*The gateway to transcription: identifying, characterizing and understanding promoters in the eukaryotic genome*"; Cell. Mol. Life Sci., 64, (2007), pp. 386 400.
Higo et al.: "*Plant cis-acting regulatory DNA elements (PLACE) database: 1999*"; Nucleic Acids Research, 1999, vol. 27, No. 1, pp. 297-300.
Kindle, Karen L.: "*High-frequency nuclear transformation of Chlamydomonas reinhardtii*"; Proc. Natl. Acad. Sci. USA, Feb. 1990, vol. 87, pp. 1228-1232.
Kindle, Karen L. et al.: "*Stable Nuclear Transformation of Chlamydomonas Using the Chlamydomonas Gene for Nitrate Reductase*"; J. Cell Biology, vol. 109 No. 6:1, Dec. 1989, pp. 2589-2601.
Lescot et al.: "*PlantCARE, a database of plant cis-acting regulatory elements and a portal to tools for in silico analysis of promoter sequences*"; Nucleic Acids Research, 2002, vol. 30, No. 1, pp. 325-327.

(Continued)

*Primary Examiner* — Deborah Crouch
*Assistant Examiner* — Magdalene Sgagias
(74) *Attorney, Agent, or Firm* — DLA Piper LLP (US)

(57) ABSTRACT

The present application provides novel regulatory elements including promoter sequences from marine microorganisms. The application further discloses DNA constructs containing these novel regulatory elements; transgenic cells, transgenic non-human organisms, and progeny containing these novel regulatory elements. Methods of modifying, producing, and using the regulatory elements are also disclosed. The regulatory elements disclosed herein are particularly suited for use in *Nannochloropsis* and other microalgae.

23 Claims, 1 Drawing Sheet

(56) References Cited

OTHER PUBLICATIONS

Liu, Qian et al.: "*Evigan: a hidden variable model for integrating gene evidence for eukaryotic gene prediction*"; Bioinformatics, vol. 24, No. 5, 2008, pp. 597-605.

Lumbreras, Victoria et al.: "*Efficient foreign gene expression in Chlamydomonas reinhardtii mediated by an endogenous intron*"; Plant Journal ,1998), 14(4), pp. 441-447.

Mendez-Alvarez et al.: "*Transformation of Chlorobium Confers the Ability to limicola by a Plasmid That Utilize Thiosulfate*"; J. Bacteriology, Dec. 1994, vol. 176:23, pp. 7395-7397.

Mogno, Ilaria et al.: "*TATA is a modular component of synthetic promoters*"; Genome Research, 2010, vol. 20, pp. 1391-1397.

Ohnuma, Mio et al.: "*Polyethylene Glycol (PEG)-Mediated Transient Gene Expression in a Red Alga, Cyanidioschyzon merolae 10D*"; Plant Cell Physiol., 2008, vol. 49(1), pp. 117-120.

Piechulla,Birgit et al.: "*Identification of tomato Lhc promoter regions necessary for circadian Expression*"; Plant Molec.Bio., 1998, vol. 38, pp. 655-662.

Poulsen, Nicole et al.: "*A new molecular tool for transgenic diatoms Control of mRNA and protein biosynthesis by an inducible promoter—terminator cassette*"; FEBS Journal, 272 (2005), pp. 3413-3423.

Qin, Yong et al.: "*Structures, folding patterns, and functions of intramolecular DNA G-quadruplexes found in eukaryotic promoter regions*"; Biochimie., Aug. 2008, vol. 90(8), pp. 1149-1171.

Quinn, Jeanette, M. et al.: "*Copper Response Element and Crr1-Dependent Ni2_-Responsive Promoter for Induced, Reversible Gene Expression in Chlamydomonas reinhardtii*"; Eukaryotic Cell, Oct. 2003, vol. 2:5, pp. 995-1002.

Radakovits, Randor et al.: "*Draft genome sequence and genetic transformation of the oleaginous alga Nannochloropis gaditana*"; Nature Communications, Feb. 21, 2012, 3:686, pp. 1-10.

Radakovits, Randor et al.: Supplementary Information—"*Draft genome sequence and genetic transformation of the oleaginous alga Nannochioropsis gaditana*"; Nature Communications, Feb. 21, 2012, 3:686, 53 pgs.

Ranjan, Rajiv et al.: "*Efficient chimeric promoters derived from full-length and sub-genomic transcript promoters of Figwort mosaic virus (FMV)*"; J. Biotechnology, 152 (2011) pp. 58-62.

Rombauts, Stephane et al.: "*PlantCARE, a plant cis-acting regulatory element Database*"; Nucleic Acids Research, 1999, vol. 27:1, pp. 295-296.

Reeder, Ronald H. et al.: "*Terminating transcription transcription in eukaryotes: lessons learned from RNA polymerase 1*"; TIBS, Dec. 1997 (22) pp. 473-477.

Schroda, Michael: "*RNA silencing in Chlamydomonas: mechanisms and tools*"; Curr Genet, (2006), vol. 49, pp. 69-84.

Shahmuradov, Ilham et al.: "*PlantProm: a database of plant promoter sequences*"; Nucleic Acids Research, 2003, vol. 31:1, pp. 114-117.

Shandilya, Jayasha et al.: "*The transcription cycle in eukaryotes: From productive initiation to RNA polymerase II recycling*"; Biochimica et Biophysica Acta 1819, (2012), pp. 391-400.

Walker, T. L. et al.: "*Characterisation of the Dunaliella tertiolecta RbcS genes and their promoter activity in Chlamydomonas reinhardtii*"; Plant Cell Rep (2005), 23, pp. 727-735.

Watt, Stephen et al.: "*urg1: A Uracil-Regulatable Promoter System for Fission Yeast with Short Induction and Repression Times*"; PLoS ONE, Jan. 2008, Issue 1, e1428, 8 pgs.

Wodniok, Sabina et al.: "*Gain and loss of polyadenylation signals during evolution of green Algae*";. BMC Evol. Biol., 2007, 7:65, 12 pgs.

Zhao, Jing et al.: "*Formation of mRNA 39 Ends in Eukaryotes: Mechanism, Regulation, and Interrelationships with Other Steps in mRNA Synthesis*"; Microbio. & Molec. Bio. Reviews, Jun. 1999, vol. 63:2, pp. 405-445.

Zhao, Tao et al.: "*Gene silencing by artificial microRNAs in Chlamydomonas*"; Plant Journal, (2009), vol. 58, pp. 157-164.

\* cited by examiner

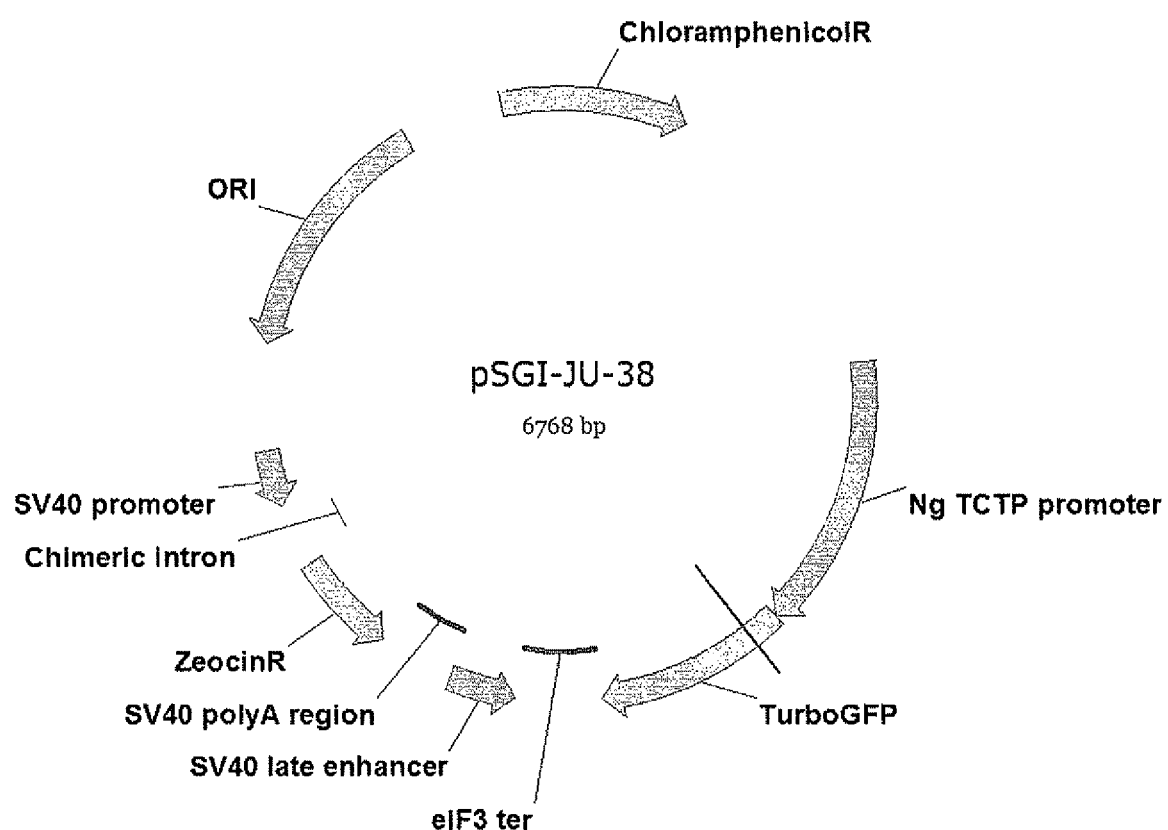

REGULATORY ELEMENTS AND USES THEREOF

CROSS REFERENCE TO RELATED APPLICATION(S)

This application is an International Patent Application which claims the benefit of priority under 35 U.S.C. §119(e) of U.S. Ser. No. 61/658,732 filed Jun. 12, 2012. The disclosure the prior application is considered part of, and is incorporated by reference in, the disclosure of this application.

FIELD OF THE INVENTION

The present application relates generally to molecular biology and genetic engineering and more specifically, to regulatory elements useful for modulating in vivo and in vitro transcription of polynucleotide molecules.

INCORPORATION OF SEQUENCE LISTING

The material in the accompanying sequence listing is hereby incorporated by reference into this application. The accompanying sequence listing text file, name SGI1590-1_Sequence Listing, was created on Jun. 11, 2013 and is 4 KB. The file can be assessed using Microsoft Word on a computer that uses Windows OS.

BACKGROUND OF THE INVENTION

Modern genetic engineering offers tremendous opportunities to develop biotech organisms with commercially desirable characteristics or traits. Particularly, recent advances in molecular biology and transgenic technologies have greatly accelerated the introduction of new genes and, hence new traits into commercial crops. The proper expression of a desirable transgene in a transgenic organism is widely considered to be a requisite requirement to achieve this goal. Nucleic acid elements having gene regulatory activity, i.e. regulatory elements such as promoters, leaders, enhancers, introns and transcription termination regions, are polynucleotide molecules which play an integral part in the overall expression of genes in living cells. Isolated regulatory elements that function in a crop of interest are therefore useful for modifying the crop's characteristics through the methods of genetic engineering.

In the field of algae biotechnology, transgenesis of algae is a complex and fast growing technology. A powerful driving force in algal transgenesis is the promising prospect of using genetically modified algae as bioreactors. In fact, non-transgenic algal biotechnology has been deployed in many technology areas including nutrition, aquaculture, production of chemicals and pharmaceuticals, etc. In particular, non-transgenic microalgae have proven their utility and tractability as a production system for therapeutic or industrial products and, in this respect, algae now seem poised to become the "green" alternative to current mammalian, yeast, insect, or even bacterial recombinant production systems. Furthermore, recent progress in algal transgenesis promises a much broader field of application in molecular farming, which is generally defined as the production of proteins or metabolites that are valuable to medicine or industry, and has become increasingly feasible with transgenic algal systems. Indeed, the ability of transgenic algae to produce high levels of recombinant antibodies, vaccines, insecticidal proteins, or bio-hydrogen has already been demonstrated in several microalgal species.

As a result, there is a continuing need for novel genetic tools and methods that would facilitate the genetic engineering of algae to further enhance their physiological properties. In particular, several microalgae have recently attracted considerable attention as being potentially suitable for algal biofuel production. However, optimization of culture conditions for selected microalgal species has been reported to be potentially a challenge, because the fatty add content of individual species and isolates can vary considerably under different environmental conditions in laboratory culture and in large-scale production field. For these reasons and others, it is of immense social, ecological and economic interests to develop novel algal strains that have enhanced nutritional value, improved resistance to biotic contaminations, and tolerance to harsh conditions such as high salinity and high temperature. Therefore, more efficient methods and systems for large-scale cultivation of microalgae are critical if algal-derived biofuels are to become a reality. If these issues can be resolved, algae will potentially represent a far more superior source of biofuel than terrestrial plants. Optimization of biofuel production in algal systems should further improve the potential of this auspicious technology in the future.

However, despite the availability of many molecular tools, the genetic modification of algae, particularly microalgae, is often constrained by an insufficient expression level or temporally nonspecific expression of the engineered transgene. In addition, while previous work has provided a number of regulatory elements that can be used to affect gene expression in transgenic algae, there is still a great need for novel regulatory elements with beneficial expression characteristics. One example of this is the need for regulatory elements capable of driving gene expression preferentially in different algal growth phases. On the other hand, there exists a need for regulatory elements capable of driving gene expression constitutively throughout cell life cycle and/or unaffected by growth conditions. Thus, the identification of novel molecular tools including genes, vectors, regulatory elements (e.g., promoters), etc. that function in various types of algae and in distinct growth phases and growth conditions will be useful in developing enhanced varieties of algae.

Furthermore, as the field of algal transgenesis develops and more genes become accessible, a greater need exists for algae transformed with multiple genes. These multiple exogenous genes typically need to be transcriptionally controlled by separate regulatory sequences. For example, some transgenes need to be expressed in a constitutive manner whereas other genes should be expressed at certain developmental stages or in specific compartments of the transgenic cell. In addition, multiple regulatory sequences are also needed in order to avoid undesirable molecular interactions which can result from using the same regulatory sequence to control more than one transgene.

SUMMARY OF THE INVENTION

Disclosed herein are isolated polynucleotide molecules having gene regulatory activity that can be used to affect expression of a heterologous nucleic acid sequence in vivo and/or in vitro. Also provided are the design, construction, and use of these polynucleotide molecules in, for example, regulating expression of polynucleotide sequences of interest, and thereby impacting various traits in transgenic cells.

Particularly, the polynucleotide molecules disclosed herein can be used to control expression of selectable markers in transformation systems.

Methods and materials useful for modulating gene expression in vivo and/or in vitro are disclosed. In particular, the present application discloses novel polynucleotide molecules having gene regulatory activity, such as novel regulatory elements from marine microorganisms. The application further discloses nucleic acid constructs containing these novel regulatory elements; transgenic cells; transgenic organisms, and progeny containing these novel regulatory elements. Methods of modifying, producing, and using the regulatory elements are also disclosed. The regulatory elements disclosed herein are particularly suited for use in *Nannochloropsis* and other microalgae.

In one aspect of the present invention, the disclosure provides isolated nucleic acid molecules comprising nucleic acid sequences that hybridize under high stringency conditions to a nucleotide sequence selected from the group consisting of SEQ ID NO: 1 through SEQ ID NO: 16; complements of the nucleotide sequences that hybridize under high stringency conditions to a nucleotide sequence selected from the group consisting of SEQ ID NO: 1 through SEQ ID NO: 16; and fragments of either.

In one embodiment of this aspect, the disclosure further provides isolated nucleic acid molecules comprising nucleic acid sequences exhibiting 70% or greater sequence identity to a nucleotide sequence selected from the group consisting of SEQ ID NO: 1 through SEQ ID NO: 16; complements of the nucleotide sequences exhibiting 70% or greater sequence identity to a nucleotide sequence selected from the group consisting of SEQ ID NO: 1 through SEQ ID NO: 16; and fragments of either.

In another embodiment of this aspect, the disclosure further provides fragments or cis-acting elements of isolated nucleic acid molecules comprising nucleic acid sequences that hybridize under high stringency conditions to a nucleotide sequence selected from the group consisting of SEQ ID NO; 1 through SEQ ID NO: 16; complements of the nucleotide sequences that hybridize under high stringency conditions to a nucleotide sequence selected from the group consisting of SEQ ID NO: 1 through SEQ ID NO: 16; and fragments of either. The disclosure further provides fragments or cis-acting elements of isolated nucleic acid molecules including nucleic acid sequences exhibiting 70% or greater sequence identity to a nucleotide sequence selected from the group consisting of SEQ ID NO: 1 through SEQ ID NO: 16; complements of the nucleotide sequences exhibiting 70% or greater sequence identity to a nucleotide sequence selected from the group consisting of SEQ ID NO: 1 through SEQ ID NO: 16; and fragments of either. In some preferred embodiments, an isolated nucleic acid molecule according to this aspect of the present invention may include one or more of the following features. The isolated nucleic acid molecule may be a promoter. The isolated nucleic acid molecule may further comprise one or more cis-acting nucleic acid element. The isolated nucleic acid molecule may further include a 5' leader sequence. The isolated nucleic acid molecule may further include a 3' untranslated region. The isolated nucleic acid molecule may further include an intron.

In another aspect, the disclosure also provides nucleic acid constructs which include a nucleic acid molecule disclosed herein that is operably linked to a heterologous nucleic acid. Particularly, in some embodiments of this aspect, the disclosure provides nucleic acid constructs that include a heterologous nucleic acid molecule operably linked to a nucleic acid molecule comprising a nucleic acid sequence that (a) hybridizes under high stringency conditions to a nucleic acid sequence selected from the group consisting of SEQ ID NO: 1 through SEQ ID NO: 16, a complement thereof or a fragment of either; or (b) exhibits 70% or greater sequence identity to a nucleic acid sequence selected from the group consisting of SEQ ID NO: 1 through SEQ ID NO: 16, a complement thereof or a fragment of either; or (c) comprises a fragment or a cis-acting element of a nucleic acid sequence according to anyone of (a) or (b) above.

In some embodiments of this aspect, the nucleic acid constructs disclosed herein are nucleic acid vectors. In some other embodiments, the heterologous nucleic acid molecule included in the nucleic acid construct is a transcribable polynucleotide molecule. In yet some other embodiments, the transcribable polynucleotide molecule is operably linked to a 3' transcription termination polynucleotide molecule.

According to some embodiments of this aspect, the transcribable polynucleotide molecule comprises a nucleic acid sequence that is involved in modulating the phenotype of a trait. In certain preferred embodiments, the trait may be abiotic stress resistance, activity of a polyketide synthase complex, bacterial disease resistance, biofuel production, biopolymer production, carbohydrate content, cell wall components, enhanced animal and human nutrition, enzyme production, flavor production, growth and development, herbicide tolerance, high protein production, isoprenoid content, modified amino acid content, modified biomass yield, modified fatty acid/oil content, modified oils production, nitrogen utilization, photosynthesis capacity, production of pharmaceutical molecules, production of pigments, or virus resistance. In a preferred embodiment, the transcribable polynucleotide molecule includes a nucleic acid sequence that is involved in modulating herbicide tolerance. In a particularly preferred embodiment, the nucleic acid sequence involved in modulating herbicide tolerance encodes acetyl coenzyme-A carboxylase (ACCase), aminoglycoside phosphotransferase, anthranilate synthase, bromoxynil resistant nitrilase, cytochrome P450-NADH-cytochrome P450 oxidoreductase, dalapon dehalogenase, glutathione reductase, glyphosate acetyl transferase, glyphosate oxidoreductase, glyphosate resistant EPSPS, hydroxyacetoacid synthase (AHAS), hydroxyphenyl pyruvate dehydrogenase (HPPD), isoprenyl pyrophosphate isomerase, lycopene cyclase, phosphinothricin acetyl transferase (PAT), phytoene desaturase, prenyl transferase, protoporphyrinogen oxidase, or superoxide dismutase (SOD).

Further provided in another aspect of the present disclosure is an isolated transgenic cell. The transgenic cell includes a nucleic acid construct comprising a nucleic acid molecule disclosed herein that is operably linked to a heterologous nucleic acid. Particularly, in some embodiments of this aspect, the heterologous nucleic acid is operably linked to a nucleic add molecule comprising a nucleic acid sequence that (a) hybridizes under high stringency conditions to a nucleic acid sequence selected from the group consisting of SEQ ID NO: 1 through SEQ ID NO: 16, a complement thereof or a fragment of either; or (b) exhibits 70% or greater sequence identity to a nucleic acid sequence selected from the group consisting of SEQ ID NO: 1 through SEQ ID NO: 16, a complement thereof or a fragment of either; or (c) comprises a fragment or a cis-acting element of a nucleic acid sequence according to anyone of (a) or (b) above. In some preferred embodiments of this aspect, such transgenic cell may be a microbial cell. In other preferred embodiments, such microbial cell is a microalgal cell. In yet some other preferred embodiments, the transgenic cell is stably transformed with the nucleic acid construct.

The disclosure further provides isolated non-human transgenic organisms containing a transgenic cell that includes a nucleic acid construct comprising a nucleic acid molecule disclosed herein that is operably linked to a heterologous nucleic acid. In some embodiments, the heterologous nucleic acid is operably linked to a nucleic acid molecule comprising a nucleic acid sequence that (a) hybridizes under high stringency conditions to a nucleic acid sequence selected from the group consisting of SEQ ID NO: 1 through SEQ ID NO: 16, a complement thereof or a fragment of either; or (b) exhibits 70% or greater sequence identity to a nucleic acid sequence selected from the group consisting of SEQ ID NO: 1 through SEQ ID NO: 16, a complement thereof or a fragment of either; or (c) comprises a fragment or a cis-acting element of a nucleic acid sequence according to anyone of (a) or (b) above. The disclosure further provides biological samples, biomass, and progeny that are derived from the transgenic organisms described herein. Also provided are compositions containing biomaterial derived from the transgenic organisms disclosed herein.

Another aspect of the present invention relates to a method for making an isolated transgenic cell. The method includes introducing into a cell a nucleic acid molecule comprising a nucleic acid sequence that (a) hybridizes under high stringency conditions to a nucleic acid sequence selected from the group consisting of SEQ ID NO: 1 through SEQ ID NO: 16, a complement thereof or a fragment of either; or (b) exhibits 70% or greater sequence identity to a nucleic acid sequence selected from the group consisting of SEQ ID NO: 1 through SEQ ID NO: 16, a complement thereof or a fragment of either; or (c) comprises a fragment or a cis-acting element of a nucleic acid sequence according to anyone of (a) or (b) above.

These and other objects and features of the invention will become more fully apparent from the following detailed description of the invention and the claims.

BRIEF DESCRIPTION OF THE DRAWINGS

FIG. 1 is a schematic representation of plasmid pSGI-JU-38 that comprises a TCTP regulatory sequence from *Nannochloropsis gaditana* (SEQ ID NO: 1) driving the expression of a TurboGFP green fluorescence protein reporter gene; a Zeocin resistance gene under control of SV40 regulatory elements; and a chloramphenicol resistance gene. ORI is a prokaryotic origin of replication.

DETAILED DESCRIPTION OF THE INVENTION

This application relates to compositions, methods and related materials to genetically transform organisms. More specifically, this application provides methods and materials useful for modulating gene expression in vivo and/or in vitro. In particular, novel polynucleotide molecules having gene regulatory activity, i.e. regulatory elements, are disclosed. Methods of modifying, producing, and using such regulatory elements are also disclosed. Further, transgenic cells, transgenic organisms, and progeny thereof containing a novel regulatory element disclosed herein, and method for preparing and using the same, are also provided.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

The singular form "a", "an", and "the" include plural references unless the context clearly dictates otherwise. For example, the term "a cell" includes one or more cells, including mixtures thereof.

"Biofuels", as used herein, refer to renewable energy sources from living organisms, such as higher plants, fungi, algae, or microorganisms. As such, biofuels can be solid, liquid or gaseous fuels derived from algal, fungal, microbial or plant materials, biomass, sugars or starches, such as ethanol or biodiesel derived from vegetable oils or algal oil, and the like. A biofuel is a fuel in its own right, but may be blended with petroleum-based fuels to generate a finished fuel. A biofuel may be used as a replacement for petrochemically-derived gasoline, diesel fuel, or jet fuel.

A "control organism" or "control cell" as used in the present invention provides a reference point for measuring changes in phenotype of the subject organism or cell, may be any suitable organism or cell. A control organism or cell may comprise, for example, (a) a wild-type organism or cell, i.e. of the same genotype as the starting material for the genetic alteration which resulted in the subject organism or cell; (b) an organism or cell of the genotype as the starting material but which has been transformed with a null construct (i.e. a construct which has no known effect on the trait of interest, such as a construct comprising a reporter gene); (c) an organism or cell which is a non-transformed segregant among progeny of a subject organism or cell; (d) an organism or cell which is genetically identical to the subject organism or cell but which is not exposed to the same treatment (e.g., herbicide treatment) as the subject organism or cell; (e) the subject organism or cell itself, under conditions in which the gene of interest is not expressed; or (f) the subject organism or cell itself, under conditions in which it has not been exposed to a particular treatment such as, for example, a herbicide or combination of herbicides and/or other chemicals. In some instances, the term "control organism" refers to an organism or cell used to compare against transgenic or genetically modified organism for the purpose of identifying a modulated phenotype in the transgenic or genetically modified organism. A "control organism" may in some cases refer to an organism that does not contain the exogenous nucleic acid present in the transgenic organism of interest, but otherwise has the same of similar genetic background as such a transgenic organism. In some other instances, an appropriate control organism or cell may have a different genotype from the subject organism or cell but may share the herbicide-sensitive characteristics of the starting material for the genetic alteration(s) which resulted in the subject organism or cell.

The term "endogenous," within the context of the current invention refers to any polynucleotide, polypeptide or protein sequence which is a natural part of a cell or organism regenerated from said cell.

"Exogenous" with respect to a nucleic acid indicates that the nucleic acid is part of a recombinant nucleic acid construct and is not in its natural environment. For example, an exogenous nucleic acid can be a sequence from one species introduced into another species, i.e., a heterologous nucleic acid. Typically, such an exogenous nucleic acid is introduced into the other species via a nucleic acid construct. An exogenous nucleic acid can also be a sequence that is native to an organism and that has been reintroduced into cells of that organism. An exogenous nucleic acid that includes a native sequence can often be distinguished from the naturally-occurring sequence by the presence of non-natural sequences linked to the exogenous nucleic acid, e.g., non-native regulatory sequences flanking a native sequence in a nucleic acid construct. In addition, stably transformed exogenous nucleic acids can be integrated at positions other than the position where the native sequence is found. It will be appreciated that an exogenous nucleic acid may have been introduced into a progenitor, and not into the cell under consideration. For example, a transgenic plant containing an exogenous nucleic acid can be the progeny of a cross between a stably transformed plant and a non-transgenic plant. Such progeny are considered to contain the exogenous nucleic add.

As used herein, "expression" refers to the process of converting genetic information of a polynucleotide into RNA through transcription, which is typically catalyzed by an enzyme, RNA polymerase, and into protein, through translation of mRNA on ribosomes "Herbicide resistance" or "herbicide tolerance", as used herein, refers to a capability of an organism or cell to grow in the presence of selective concentrations of an herbicidal compound. As used herein, the term "tolerance" is broader than the term "resistance", and includes "resistance" as defined herein as an improved capacity of a particular organism to withstand the various degrees of herbicidally induced injury that typically result in wild-type organism of the same genetic background at the same herbicidal dose. The term "selective concentration" refers to a concentration of an inhibitor or antibiotic compound, for example, an herbicide, which is capable of inhibiting the metabolism, growth, or multiplication of a wild-type cell or organism. Such a wild-type organism, as well as progeny thereof, is referred to as a "sensitive" organism or cell. In relation to particular enzymes or proteins, "sensitive" indicates that the enzyme or protein is susceptible to specific inhibition by a particular inhibiting compound, for example, an antibiotic or herbicide. In relation to particular enzymes or proteins, "resistant" indicates that the enzyme or protein, as a result of a different chemical structure, expresses activity in the presence of a selective concentration of a specific inhibitor which inactivates sensitive variants of the enzyme or protein.

Heterologous polynucleotides as used herein are those that are not operably linked or are not contiguous to each other in nature. For example, a promoter from *Schizochytrium* sp. is considered heterologous to a *Nannochloropsis* coding region sequence. Further, a promoter from a gene encoding a hexose kinase from *Nannochloropsis* is considered heterologous to a sequence encoding a hexose transporter from the same source organism, i.e. *Nannochloropsis*. Regulatory element sequences, such as untranslated regions (UTRs) or 3' end termination sequences that do not originate in nature from the same gene as the coding sequence, are considered heterologous to said coding sequence. Elements operably linked in nature and contiguous to each other are not heterologous to each other. On the other hand, these same elements remain operably linked but become heterologous if other filler sequence is placed between them. Thus, the promoter and coding sequences of a *Nannochloropsis* gene expressing, for example, a hexose transporter are not heterologous to each other, but the promoter and coding sequence of a *Nannochloropsis* gene operably linked in a novel manner are heterologous. "Heterologous polypeptide" as used herein refers to a polypeptide that is not a naturally-occurring polypeptide in a host cell, e.g., a transgenic *Nannochloropsis* microorganism transformed with and expressing the coding sequence for a fatty acid transporter from a *Schizochytrium* microorganism or from a plant.

The term "misexpression" as used herein refers to an increase or decrease in the transcription of a coding region into a complementary RNA sequence as compared to the parental wild-type, for example, plant or microorganism. This term also encompasses expression of a gene or coding region for a different time period (i.e. temporal misexpression) as compared to the wild-type and/or from a non-natural location within the parental genome (e.g., ectopic expression).

As used herein, "modulation" of the level of a compound or constituent refers to the change in the level of the indicated compound or constituent that is observed as a result of expression of, or transcription from, an exogenous nucleic acid in a cell or an organism. The change in level is measured relative to the corresponding level in control cell or organism.

"Polypeptide" as used herein refers to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. Full-length polypeptides, truncated polypeptides, point mutants, insertion mutants, splice variants, chimeric proteins, and fragments thereof are encompassed by this definition.

As used herein, "progeny" includes descendants of a particular plant or plant line. Progeny of an instant plant include seeds formed on $F_1$, $F_2$, $F_3$, $F_4$, $F_5$, $F_6$ and subsequent generation plants, or seeds formed on $BC_1$, $BC_2$, $BC_3$, and subsequent generation plants, or seeds formed on $F_1BC_1$, $F_1BC_2$, $F_1BC_3$, and subsequent generation plants. The designation $F_1$ refers to the progeny of a cross between two parents that are genetically distinct. The designations $F_2$, $F_3$, $F_4$, $F_5$ and $F_6$ refer to subsequent generations of self- or sib-pollinated progeny of an $F_1$ plant.

The term "selectable genetic marker", or its abbreviated form "selectable marker", as used herein refers to a nucleotide sequence which, when incorporated into the genome of an organism, allows differentiating that organism and its progeny from organisms lacking the selectable genetic marker. Non-limiting exemplifications of selectable genetic markers include those, when incorporated into the genome of an organism, allow growth of that organism and its progeny under conditions which inhibit growth of the organism lacking the selectable genetic markers. For example, a gene which encodes an enzyme that is resistant to specific inhibition by a particular antibiotic compound, such as a herbicide, can function as a selectable genetic marker by allowing an organism, such as a plant or an alga, to grow and propagate in the presence of a selective concentration of the compound. A second nucleic acid fragment, controlling a property which is difficult to assay, can be covalently linked to the selectable genetic marker, in which case the presence of the selectable marker, indicated by growth of an organism under selective conditions, can be used to detect an organism containing the second nucleic acid fragment.

In the context of the present invention, a "translational start site" is usually an ATG or AUG in the cDNA transcript, more usually the first ATG or AUG. A single protein encoding transcript, however, may have multiple translational start sites.

"Transcription start site" is used in the present invention to describe the point at which transcription is initiated. This point is typically located about 25 nucleotides downstream from a TFIID binding site, such as a TATA box. Transcription can initiate at one or more sites within the gene, and a single gene may have multiple transcriptional start sites, some of which may be specific for transcription in a particular cell-type or tissue.

As used herein, "transgenic organism" refers to an organism which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. When referring to a plant, "transgenic" is used herein to include any cell, cell line, callus, tissue, plant part or plant, the genotype of which has been altered by the presence of heterologous nucleic acid. The term "transgenic" includes those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally-occurring events such as random cross-fertilization, non-recombinant viral infection, non-recombinant bacterial transformation, non-recombinant transposition, or spontaneous mutation.

Variant: when referring to polypeptides and nucleic acids, the term "variant" is used herein to denote a polypeptide, protein or polynucleotide molecule with some differences, generated synthetically or naturally, in their base or amino acid sequences as compared to a reference polypeptide or polynucleotide, respectively. For example, these differences include substitutions, insertions, deletions or any desired combinations of such changes in a reference polypeptide or polynucleotide. Polypeptide and protein variants can further consist of changes in charge and/or post-translational modifications (such as glycosylation, methylation, phosphorylation, etc.) "Functional variants" of the regulatory polynucleotide sequences are also encompassed by the compositions of the present invention. Functional variants include, for example, the native regulatory polynucleotide sequences of the invention having one or more nucleotide substitutions, deletions or insertions and which can drive expression of an operably-linked polynucleotide sequence under conditions similar to those under which the native promoter is active. Functional variants of the invention may be created by site-directed mutagenesis, induced mutation, or may occur as allelic variants (polymorphisms).

As used herein, the term "yield" refers to the amount of harvestable biomaterial or biomaterial-derived product, and is normally defined as the measurable produce of economic value of a crop. For example, for plant and algae crops, "yield" also means the amount of harvested material per acre or unit of production. Yield may be defined in terms of quantity or quality. The harvested material may vary from crop to crop, for example, it may be plant seeds, above ground biomass, roots, fruits, cotton fibers, any other part of the plant, or any plant-derived product which is of economic value. The term "yield" also encompasses yield potential, which is the maximum obtainable yield. Yield may be dependent on a number of yield components, which may be monitored by certain parameters. These parameters are well known to persons skilled in the art and vary from crop to crop. The term "yield" also encompasses harvest index, which is the ratio between the harvested biomass over the total amount of biomass.

All publications and patent applications mentioned in this specification are herein incorporated by reference to the same extent as if each individual publication or patent application was specifically and individually indicated to be incorporated by reference.

No admission is made that any reference constitutes prior art. The discussion of the references states what their authors assert, and the applicants reserve the right to challenge the accuracy and pertinence of the cited documents. It will be clearly understood that although a number of publications are referred to herein; this reference does not constitute an admission that any of these documents forms part of the common general knowledge in the art.

The discussion of the general methods given herein is intended for illustrative purposes only. Other alternative methods and embodiments will be apparent to those of skill in the art upon review of this disclosure.

Polynucleotide Molecules of the Invention

In one aspect of the present invention, the disclosure provides novel isolated nucleic add molecules, nucleic acid molecules that hybridize to these nucleic acid molecules, nucleic acid molecules that exhibit substantial sequence identity to these nucleic acid molecules, and nucleic acid molecules including a fragment or a cis-acting element of these nucleic acid molecules. Additional embodiments of the present application further include nucleic acid constructs, such as nucleic acid vectors, that comprise a nucleic acid molecule disclosed herein.

The terms "polynucleotide sequence" and "nucleic acid sequence" as used herein interchangeably refer to the sequence of a polynucleotide molecule. The nomenclature for nucleotide bases as set forth in 37 CFR §1.822 is used herein.

The polynucleotides of the present invention will preferably be "biologically active" with respect to either a structural attribute, such as the capacity of a nucleic acid molecule to hybridize to another nucleic acid molecule, or the ability of a polynucleotide sequence to be recognized and bound by a transcription factor (or to compete with another nucleic acid molecule for such binding). Alternatively, such an attribute may be catalytic and thus involve the capacity of the molecule to mediate a biochemical interaction or response.

As described in detail elsewhere herein, the nucleic acid molecules according to the present invention may be present in a chimeric, modular, or hybrid regulatory expression element.

The nucleic acid molecules of the present invention may also be recombinant. As used herein, the term recombinant means any molecule (e.g. DNA, RNA, etc.), that is, or results, however indirect, from human manipulation of a polynucleotide.

Preferably, an isolated nucleic acid molecule of the present invention is produced using recombinant DNA technology (e.g., polymerase chain reaction (PCR) amplification, cloning, etc.) or chemical synthesis. Isolated nucleic acid molecules of the present invention include natural nucleic acid molecules and homologs thereof, including, but not limited to, natural allelic variants and modified nucleic acid molecules in which nucleotides have been inserted, deleted, and/or substituted, in such a manner that such modifications provide the desired effect on the biological activity of the regulatory elements as described herein.

A nucleic acid molecule homolog can be produced using a number of methods known to those skilled in the art (see, for example, Sambrook et al., In: *Molecular Cloning, A Laboratory Manual*, 2nd Edition, Cold Spring Harbor Press, Cold Spring Harbor, N.Y. (1989)). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, PCR amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologs can be selected from a mixture of modified nucleic acids by screening for the promoter activity of the nucleic acid molecules and/or by hybridization with a wild-type promoter sequence.

Nucleic acid molecules of the present invention include nucleic acid sequences that are preferably between about 0.01 Kb and about 50 Kb, more preferably between about 0.1 Kb and about 25 Kb, between about 0.1 Kb and about 1 Kb, even more preferably between about 0.5 Kb and about 10 Kb, and most preferably between about 1 Kb and about 10 Kb, about 2 Kb and about 7 Kb, about 3 Kb and about 6 Kb, about 2 Kb and about 4 Kb, about 2 Kb and about 5 Kb, about 0.5 Kb and about 5 Kb, about 0.5 Kb and about 3 Kb, about 0.5 Kb and about 1 Kb, or about 1 Kb and about 2 Kb.

The terms "nucleic acid molecule" and "polynucleotide molecule" are used interchangeably herein, and refer to both DNA and RNA molecule, including cDNA, genomic DNA, synthetic DNA, and DNA or RNA containing nucleic acid analogs. Polynucleotides can have any three-dimensional structure. Polynucleotides can be natural-occurring or synthetic origin. A nucleic acid molecule can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, nucleic acid probes and nucleic acid primers. A polynucleotide may contain unconventional or modified nucleotides.

By the term "isolated", it is meant that the molecule referenced is not in its native environment, i.e. not normally found in the genome of a particular host cell. An "isolated" or "substantially purified" nucleic acid molecule, or biologically active portion thereof, is substantially free of other cellular material or culture medium when produced by recombinant techniques, or substantially free of chemical precursors or other chemicals when chemically synthesized. The term "substantially purified", as used herein, refers to a molecule separated from substantially all other molecules normally associated with it in its native state. More preferably a substantially purified molecule is the predominant species present in a preparation that is, or results, however indirect, from human manipulation of a polynucleotide or polypeptide. A substantially purified molecule may be greater than 60% free, preferably 75% free, more preferably 90% free, and most preferably 95% free from the other molecules (exclusive of solvent) present in the natural mixture. The term "substantially purified" is not intended to encompass molecules present in their native state. Thus, an "isolated" nucleic acid preferably is free of sequences that naturally flank the nucleic acid (i.e., sequences located at the 5' and 3' ends of the nucleic acid) in the cell of the organism from which the nucleic acid is derived. Thus, "isolated nucleic acid" as used herein includes a naturally-occurring nucleic acid, provided one or both of the sequences immediately flanking that nucleic acid in its naturally-occurring genome is removed or absent. Thus, an isolated nucleic acid includes, without limitation, a nucleic acid that exists as a purified molecule or a nucleic acid molecule that is incorporated into a vector or a virus. A nucleic acid existing among hundreds to millions of other nucleic acids within, for example, cDNA libraries, genomic libraries, or gel slices containing a genomic DNA restriction digest, is not to be considered an isolated nucleic acid. For purposes of the present disclosure, "isolated" when used to refer to polynucleotide molecules also excludes isolated chromosomes. For example, in various embodiments, the isolated regulatory polynucleotide molecule can contain less than about 5 kb, 4 kb, 3 kb, 2 kb, 1 kb, 0.5 kb, or 0.1 kb of nucleotide sequences that naturally flank the nucleic acid molecule in the cell from which the nucleic acid is derived.

As used herein, "operably linked" is intended to mean a functional linkage between two or more sequences. For example, an operably linkage between a regulatory sequence (e.g., promoter) and a transcribable polynucleotide molecule, such as a gene of interest is functional link that allows for expression of the polynucleotide of interest, where the polynucleotide molecules are so arranged that the regulatory sequence affects the function of the transcribable polynucleotide molecule. In this sense, the term "operably linked" refers to the positioning of a regulatory region and a coding sequence to be transcribed so that the regulatory region is effective for regulating transcription or translation of the coding sequence of interest. For example, to operably link a coding sequence and a regulatory region, the translation initiation site of the translational reading frame of the coding sequence is typically positioned between one and about fifty nucleotides downstream of the regulatory region. A regulatory region can, however, be positioned as much as about 5,000 nucleotides upstream of the translation initiation site, or about 2,000 nucleotides upstream of the transcription start site.

When used to refer to the joining of two protein coding regions, by "operably linked" is intended that the coding regions are in the same reading frame. When used to refer to the effect of an enhancer, "operably linked" indicated that the enhancer increases the expression of a particular polypeptide or polynucleotides of interest. Where the polynucleotide or polynucleotides of interest encode a polypeptide, the encoded polypeptide is produced at an elevated level. It is to be understood that the term "operably linked", as used herein, includes functional linkage between polynucleotide sequences that may or may not be part of a single contiguous polynucleotide molecule and may or may not be adjacent. For example, a promoter is operably linked to a gene of interest if the promoter regulates or mediates transcription of the gene of interest in a cell.

As used herein, the term "transcribable polynucleotide molecule" refers to any polynucleotide molecule capable of being transcribed into an RNA molecule, including but not limited to coding sequences of polypeptides (e.g. transgenes), interfering RNA molecules (e.g. RNAi), and ribosomal ribonucleic acid (rRNA). When used in reference to a protein coding sequence, the term "transcribable polynucleotide molecule" is used interchangeably with the terms "coding sequence" and "structural sequence", and refers to a physical structure comprising an orderly arrangement of nucleotides. The nucleotides are arranged in a series of nucleotide triplets that each form a codon. Each codon encodes for a specific amino acid. Thus the coding sequence, structural sequence, and transcribable polynucleotide sequence encode a series of amino acids forming a protein, polypeptide, or peptide sequence. The coding sequence, structural sequence, and transcribable polynucleotide sequence may be contained, without limitation, within a larger nucleic acid molecule, vector, etc. In addition, the orderly arrangement of nucleic acids in these sequences may be depicted, without limitation, in the form of a sequence listing, figure, table, electronic medium, and the like.

Determination of Sequence Similarity Using Hybridization Techniques

Nucleic acid molecules or fragments thereof of the present invention are capable of specifically hybridizing to other nucleic acid molecules under certain circumstances. Nucleic acid hybridization is a technique well known to those of skill in the art of DNA manipulation. The hybridization properties of a given pair of nucleic acids are an indication of their similarity or identity.

The term "hybridization", as used herein, refers generally to the ability of nucleic acid molecules to join via complementary base strand pairing. Such hybridization may occur when nucleic acid molecules are contacted under appropriate conditions and/or circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, nucleic acid molecules are said to exhibit "complete complementarity" when every nucleotide of one of the molecules is complementary to its base pairing partner nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Nucleic acid molecules that hybridize to other nucleic acid molecules, e.g., at least under low stringency conditions are said to be "hybridizable cognates" of the other nucleic acid molecules. Conventional stringency conditions are described by Sambrook et al., 1989, supra), and by Haymes et al, In: *Nucleic Acid Hybridization, A Practical Approach*, IRL Press, Washington, D.C. (1985). Departures from complete complementarity are therefore permissible, as long as such departures do not completely preclude the capacity of the molecules to form a double-stranded structure. Thus, in order for a nucleic acid molecule or fragment thereof of the present invention to serve as a primer or probe it needs only be sufficiently complementary in sequence to be able to form a stable double-stranded structure under the particular solvent and salt concentrations employed.

Appropriate stringency conditions which promote DNA hybridization include, for example, 6.0× sodium chloride/sodium citrate (SSC) at about 45° C., followed by a wash of 2.0×SSC at about 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. These conditions are known to those skilled in the art, or can be found in *Current Protocols in Molecular Biology*, John Wiley & Sons, N.Y. (1989), 6.3.1-6.3.6. For example, low stringency conditions may be used to select nucleic acid sequences with lower sequence identities to a target nucleic acid sequence. One may wish to employ conditions such as about 0.15 M to about 0.9 M sodium chloride, at temperatures ranging from about 20° C. to about 55° C. High stringency conditions may be used to select for nucleic acid sequences with higher degrees of identity to the disclosed nucleic acid sequences (Sambrook et al., 1989, supra). In one embodiment of the present invention, high stringency conditions involve nucleic acid hybridization in about 2×SSC to about 10×SSC (diluted from a 20×SSC stock solution containing 3 M sodium chloride and 0.3 M sodium citrate, pH 7.0 in distilled water), about 2.5× to about 5×Denhardt's solution (diluted from a 50× stock solution containing 1% (w/v) bovine serum albumin, 1% (w/v) ficoll, and 1% (w/v) polyvinylpyrrolidone in distilled water), about 10 mg/mL to about 100 mg/ml, fish sperm DNA, and about 0.02% (w/v) to about 0.1% (w/v) SDS, with an incubation at about 50° C. to about 70° C. for several hours to overnight. High stringency conditions are preferably provided by 6×SSC, 5×Denhardt's solution, 100 mg/mL fish sperm DNA, and 0.1% (w/v) SDS, with incubation at 55×C for several hours. Hybridization is generally followed by several wash steps. The wash compositions generally comprise 0.5×SSC to about 10×SSC, and 0.01% (w/v) to about 0.5% (w/v) SDS with a 15-min incubation at about 20° C. to about 70° C. Preferably, the nucleic acid segments remain hybridized after washing at least one time in 0.1×SSC at 65° C.

According to some embodiments of the present application, nucleic acid molecules of the present invention preferably comprise a nucleic acid sequence that hybridizes, under low or high stringency conditions, to a nucleic acid sequence selected from the group consisting of SEQ ID NO: 1 through SEQ ID NO: 16, or any complements thereof, or any fragments thereof, or any cis-acting elements thereof.

Analysis of Sequence Similarity Using Identity Scoring

Nucleic acid molecules or fragments thereof of the present invention encompass those exhibiting substantial sequence identities to the nucleic acid sequences disclosed herein. As used herein "sequence identity" refers to the extent to which two optimally aligned polynucleotide are invariant throughout a window of alignment of components, e.g., nucleotides. An "identity fraction" for aligned segments of a test sequence and a reference sequence is the number of identical components which are shared by the two aligned sequences divided by the total number of components in reference sequence segment, i.e., the entire reference sequence or a smaller defined part of the reference sequence.

"Percentage of sequence identity" or "percent sequence identity", as used herein, refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. Percent sequence identity is determined by comparing two optimally locally aligned sequences over a comparison window defined by the length of the local alignment between the two sequences. The polynucleotide sequences in the comparison window may comprise additions or deletions (e.g., gaps or overhangs) as compared to the reference sequence (which does not comprise additions or deletions) for optimal alignment of the two sequences. Local alignment between two sequences only includes segments of each sequence that are deemed to be sufficiently similar according to a criterion that depends on the algorithm used to perform the alignment (e.g. BLAST). The percentage identity is calculated by determining the number of positions at which the identical nucleic acid base occurs in both sequences to yield the number of matched positions, dividing the number of matched positions by the total number of positions in the window of comparison and multiplying the result by 100. Optimal alignment of sequences for aligning a comparison window are well known to those skilled in the art and may be conducted by such as the local homology algorithm of Smith and Waterman (*Add. APL. Math.* 2:482, 1981), by the global homology alignment algorithm of Needleman and Wunsch (*J Mol. Biol.* 48:443, 1970), by the search for similarity method of Pearson and Lipman (*Proc. Natl. Acad. Sci.* (USA) 85: 2444, 1988), by heuristic implementations of these algorithms such as, GAP, BESTFIT, FASTA, and TFASTA available as part of the GCG™ Wisconsin Package™ (Genetics Computer Group, Accelrys Inc., Burlington, Mass.), by heuristic implementations of these algorithms such as NCBI BLAST, WU-BLAST, BLAT, SIM, BLASTZ, or by manual inspection. An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Query nucleic acid sequences were typically searched against subject nucleic acid sequences residing in public or proprietary databases. Such searches were done using the National Center for Biotechnology Information Basic Local Alignment Search Tool (NCBI BLAST v 2.18) program. The NCBI BLAST program is available on the internet from the National Center for Biotechnology Information (blast.ncbi.nlm.nih.gov/Blast.cgi). Typically the following parameters for NCBI BLAST were used: Filter options were set to "default", the Comparison Matrix was set to "BLOSUM62", the Gap Costs were set to "Existence: 11, Extension: 1", the Word Size was set to 3, the Expect (E threshold) was set to 1e-3, and the minimum length of the local alignment was set to 50% of the query sequence length.

Given that two sequences have been identified for comparison, GAP and BESTFIT programs are preferably employed to determine their optimal alignment. For this purpose, the percent of sequence identity is preferably determined using the BESTFIT or GAP program of the Sequence Analysis Software Package™ (Version 10; Genetics Computer Group, Inc., Madison, Wis.). GAP utilizes the algorithm of Needleman and Wunsch (Needleman and Wunsch, *J. Mol. Biol.* 48:443-453, 1970) to find the alignment of two sequences that maximizes the number of matches and minimizes the number of gaps. BESTFIT performs an optimal alignment of the best segment of similarity between two sequences and inserts gaps to maximize the number of matches using the local homology algorithm of Smith and Waterman (Smith and Waterman, *Adv. Applied Math.*, 2:482-489, 1981, Smith et al., *Nucl. Acids Res.* 11:2205-2220, 1983). The percent identity is most preferably determined using the BESTFIT program. Typically, the default values of 5.00 for gap weight and 0.30 for gap weight length are used. The term "substantial sequence identity" between polynucleotide sequences refers to polynucleotide comprising a sequence that has at least 50% sequence identity, preferably at least 70%, preferably at least 80%, more preferably at least 85%, more preferably at least 90%, even more preferably at least 95%, and most preferably at least 96%, 97%, 98% or 99% sequence identity compared to a reference sequence using the programs. Thus, according to one embodiment of the invention are polynucleotide molecules that have at least 50% sequence identity, preferably at least 70%, preferably at least 80%, more preferably at least 85%, more preferably at least 90%, even more preferably at least 95%, and most preferably at least 96%, 97%, 98% or 99% sequence identity with a polynucleotide sequence described herein. Polynucleotide molecules that are capable of regulating transcription of operably linked transcribable polynucleotide molecules and have a substantial percent sequence identity to the polynucleotide sequences of the polynucleotide molecules provided herein are encompassed within the scope of this invention.

"Homology" refers to the level of similarity between two or more nucleic acid sequences in terms of percent of positional identity (i.e., sequence similarity or identity). Homology also refers to the concept of similar functional properties among different nucleic acids. In addition, pairwise sequence homology or sequence similarity, as used herein refers to the percentage of residues that are similar between two sequences aligned.

In an alternative embodiment, the nucleic acid molecules comprises a nucleic acid sequence that exhibits 70% or greater identity, and more preferably at least 80% or greater, 85% or greater, 87% or greater, 88% or greater, 89% or greater, 90% or greater, 91% or greater, 92% or greater, 93% or greater, 94% or greater, 95% or greater, 96% or greater, 97% or greater, 98% or greater, or 99% or greater identity to a nucleic acid molecule selected from the group consisting of SEQ ID NO: 1 through SEQ ID NO: 16 in the Sequence Listing, any complements thereof, any fragments thereof, or any cis-acting elements thereof. The nucleic acid molecule preferably comprises a nucleic acid sequence that exhibits a 80% or greater sequence identity with a polynucleotide selected from the group consisting of SEQ ID NO: 1 through SEQ ID NO: 16 in the Sequence Listing, any complements thereof, any fragments thereof, or any cis-acting elements thereof. The nucleic acid molecule more preferably comprises a nucleic acid sequence that exhibits an 90% or greater sequence identity with a polynucleotide selected from the group consisting of SEQ ID NO: 1 through SEQ ID NO: 16 in the Sequence Listing, any complements thereof, any fragments thereof, or any cis-acting elements thereof. The nucleic acid molecule most preferably comprises a nucleic acid sequence that exhibits an 95% or greater sequence identity with a polynucleotide selected from the group consisting of SEQ ID NO: 1 through SEQ ID NO: 16 in the Sequence Listing, any complements thereof, any fragments thereof, or any cis-acting elements thereof.

For purposes of this invention, "percent identity" may also be determined using BLASTX version 2.0 for translated nucleotide sequences and BLASTN version 2.0 for polynucleotide sequences. In a preferred embodiment of the present invention, the presently disclosed gene regulatory sequences comprise nucleic acid molecules or fragments having a BLAST score of more than 200, preferably a BLAST score of more than 300, and even more preferably a BLAST score of more than 400 with their respective homologs.

Gene Regulatory Elements

In both eukaryotes and prokaryotes, expression of individual genes is finely coordinated for the proper functioning of biological processes. This coordination can be achieved both at the transcriptional and post-transcriptional levels. In fact, different gene subsets are required for the completion of different steps in an organism's development. Therefore, not all genes are turned on at all times during the life cycle of an organism. Some general types of gene expression regulation can be described: (1) temporal regulation, in which a gene is only expressed at a specific time in development (for example, during sporulation); (2) spatial regulation, in which a gene is only expressed in specific cell organelles (for example, mitochondria or chloroplast) or in specific cell types in higher plants (for example, seed storage proteins); (3) regulation of gene expression level; and (4) induction of gene expression in response to one or more stimuli. The regulation of many genes, however, may fall into more than one regulation mechanism. For example, some photosynthetic genes are only expressed in the chloroplast, but their expression is typically tightly regulated by various light conditions, such as light intensity and light quality.

Furthermore, because the binding of RNA polymerase transcription machineries to promoter sequences is typically a key step in gene expression, it follows that gene regulatory elements and sequences may exist in the promoter that control each of the above expression patterns. Indeed, many types of regulatory sequences are known to affect gene transcription in connection with RNA polymerase machineries. For example, well-known examples of long-range effectors include transcriptional enhancers, such as enhancers from simian virus 40 (SV40), that can stimulate transcription from a promoter tens of thousands of base pairs away, whereas more proximal regulatory elements include promoters, UTRs, and introns. Typically, transcription initiates at the cap site that encodes the first nucleotide of the first exon of an mRNA. For many genes, particularly those encoding abundantly expressed proteins, a cis-acting element commonly known as TATA box, which is located approximately 25-30 base pairs upstream from the cap site, directs RNA polymerase to the start site.

As described in detail elsewhere herein, several promoter-proximal elements, which are often located roughly within the first 200 base pairs upstream of the cap site, are capable of stimulating gene transcription.

In addition, features of the untranslated regions of mRNAs that control their translation, degradation, and localization typically include stem-loop structures, upstream initiation codons and open reading frames, internal ribosome entry sites and various cis-acting elements that are bound by RNA-binding proteins.

In one aspect of the present invention, this disclosure provides the composition and utility of nucleic acid molecules comprising regulatory element sequences identified from *Nannochloropsis* sp. These regulatory element sequences may comprise promoters, cis-elements, enhancers, terminators, or introns. Regulatory elements according to the present invention may be isolated or identified from untranslated regions (UTRs) from a particular protein-encoding polynucleotide.

As described in detail elsewhere herein, the nucleic acid molecules according to the present invention may be present in a chimeric, mocular, or hybrid regulatory expression element. One skilled in the art would know various promoters, introns, enhancers, transit peptides, targeting signal sequences, 5' and 3' untranslated regions (UTRs), as well as other molecules involved in the regulation of gene expression that are useful in the design of effective algal and/or plant expression vectors, such as those disclosed, for example, in U.S. Pat. No. 7,449,568 and U.S. Pat. No. 7,816,510; in U.S. Patent Publication Nos. US20030140364A1; US20090317904A1; U520100129394A1; US20100210832A1; and US20110300633A1.

The term "regulatory region" or "regulatory element", as used in the present application, refers to a polynucleotide having gene regulatory activity. The term "regulatory element" is intended to mean a series of nucleotides that determines if, when, and at what level a particular gene is expressed. Typically, the regulatory DNA sequences specifically interact with regulatory proteins or other proteins. The term "regulatory activity", as used herein in reference to a polynucleotide molecule, is intended to mean the ability of the polynucleotide to affect transcription or translation initiation and rate, and stability and/or mobility of a transcription or translation product of an operably linked transcribable polynucleotide molecule. As described in further detail below, an isolated polynucleotide molecule having regulatory activity may provide temporal or spatial expression, or modulate levels and rates of expression of the operably linked polynucleotide molecule. It is also understood that polynucleotide sequences having gene regulatory activity, or regulatory sequences, according to the present invention need not be of naturally-occurring sequences, and include but are not limited to promoter sequences, enhancer sequences, repressor elements, protein recognition sites, inducible elements, protein binding sequences, 5' and 3' untranslated regions (UTRs), leaders, transcriptional start sites, transcription termination sequences, polyadenylation sequences, introns, and the like. Such polynucleotide molecules having gene regulatory activity play an integral part in the overall expression of genes in living cells. Isolated regulatory elements and/or regions that function in a host cell are therefore useful for the modification of characteristics and phenotypes of the host cell through the methods of genetic engineering.

Promoters

Among the gene expression regulatory elements characterized to date, the promoter is considered to play a central role. Typically along the promoter, the transcription machinery is assembled with basal transcription factors, followed by initiation of transcription. This early step is often rate-limiting relative to subsequent stages of protein production, including transcription elongation and termination. Transcription initiation at the promoter may be regulated in several ways which are typically mediated by multiple transcriptional regulatory elements and their cognate transcription factors. For example, a promoter may be induced by the presence of a particular compound or external stimuli, express a gene only in a specific cell type, express a gene during a specific stage of development, or constitutively express a gene. Thus, transcription of a transgene may be regulated by operably linking the coding sequence to promoters with different regulatory characteristics. Accordingly, regulatory elements such as promoters play a pivotal role in enhancing the nutritional, economic, or commercial value of crops, e.g., algae and plants.

A "promoter", as used herein, refers to a polynucleotide molecule that is involved in recognition and binding of RNA polymerase (I, II, or III) and other proteins such as transcription factors, which are trans-acting protein factors that regulate transcription, to initiate transcription of an operably linked transcribable polynucleotide molecule. Promoters of the present invention may contain one or more of the following elements: a CAAT, a GC, or a TATA cis-acting element. Moreover, as described in detail below, the promoters of the present invention may contain one or more cis-acting elements in addition to a GC, CAAT and a TATA box. Promoters may be defined by their temporal, spatial, or developmental expression pattern. A promoter may be isolated using a genomic copy of a gene or a sequence of the 5' untranslated region (5' UTR) of its cDNA, using a variety of well-known molecular biology techniques. Alternately, promoters may be synthetically produced or manipulated based on non-coding DNA elements. As such, promoters need not be of naturally-occurring sequences. In addition, it will be understood that such promoters can be native or non-native, and thus need not be derived from the target host cell or host organism.

A promoter can be used as a 5' regulatory element for modulating expression of a particular gene, or genes operably associated thereto. When operably lined to a transcribable polynucleotide molecule, a promoter typically causes the transcribable polynucleotide molecule to be transcribed in a manner that is similar to that of which the promoter is normally associated. Promoters may themselves include sequences produced through the manipulation of known regulatory elements to produce artificial, hybrid, modular, or chimeric promoters. Such promoters can also combine heterologous sub-elements such as cis-acting elements or enhancer domains from one or more promoters that effect the transcription of operably linked polynucleotides. For example, a promoter may additionally comprise other protein recognition sequences generally positioned upstream or 5' to the TATA box, referred to as upstream promoter elements, which influence the transcription initiation rate and further include elements which impact spatial and temporal expression of the operably linked nucleotide sequence. It is generally recognized that having identified the nucleotide sequences for the promoter regions disclosed herein, it is within the state of the art to isolate and identify further regulatory elements in the 5' region upstream from a particular promoter region. Thus the promoter regions disclosed herein may comprise upstream regulatory elements such as those responsible for spatial and temporal activity of the promoters and may include activator sequences, repressor sequences, inducible response elements for transcriptional regulatory proteins, ribosomal binding sites, transcriptional start and stop sequences, translational start and stop sequences, and the like.

Thus, the design, construction, and use of chimeric, modular, or hybrid promoter comprising at least one cis-acting element of SEQ ID NOs: 1-16 for modulating the expression of operably linked polynucleotide sequences is encompassed by the present invention.

Cis-Acting Elements

As used herein, the term "cis-acting element" refers to a cis-acting transcriptional regulatory element which confers an aspect of the overall control of gene expression. In general, cis-acting elements are believed to affect DNA topology, producing local conformations that selectively allow or restrict access of RNA polymerase to the DNA template or that facilitate selective opening of the double helix at the site of transcriptional initiation. Many cis-acting elements may function to interact with transcription factors.

Cis-acting elements occur within the 5' UTR associated with a particular coding sequence, and are often found within, but are not limited to promoters, and promoter-modulating sequences (inducible elements). Examples of cis-acting elements in the 5'UTR associated with a polynucleotide coding sequence include, but are not limited to, promoters, repressors, and enhancers.

Cis-acting element can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays well known to the skilled artisan; or by DNA sequence similarity analysis with known cis-acting element motifs by conventional DNA sequence comparison methods such as, for example, those described herein. The fine structure of a cis-acting element can be further studied by mutagenesis (or substitution) of one or more nucleotides or by other conventional methods well known in molecular genetics and molecular biology. Cis-acting elements can be obtained by chemical synthesis or by isolation from promoters that include such elements, and they can be synthesized with additional flanking nucleotides that contain useful restriction enzyme sites to facilitate subsequence manipulation. Furthermore, cis-acting elements can be identified using known cis-acting elements as a target sequence or target motif in various BLAST-based computer programs.

In one embodiment, the nucleic acid molecules of the present invention comprise multiple cis-acting elements each of which confers a different aspect to the overall control of gene expression. In a preferred embodiment, cis-acting elements from the polynucleotide molecules of SEQ ID NOs: 1-16, are identified using computer programs designed specifically to identify cis-acting elements, domains, or motifs within sequences. Cis-elements may either positively or negatively regulate gene expression, depending on the conditions. The present invention therefore encompasses cis-acting elements of the disclosed nucleic acid molecules.

In one embodiment, promoters of the present invention may include homologs of cis-acting elements known to effect gene regulation and that show sequence homology with the promoter sequences of the present invention.

In one embodiment, a regulatory region according to the present invention can contain conserved regulatory motifs. Such a regulatory region can be any one of the sequences set forth in SEQ ID NO: 1 through SEQ ID NO: 16, or a regulatory region having a nucleotide sequence that deviates from any one of the sequences set forth in SEQ ID NO: 1 through SEQ ID NO: 16, while retaining the ability to direct expression of an operably linked nucleic acid. For example, a regulatory region can contain a CAAT box or a TATA box. A CAAT box is a conserved nucleotide sequence involved in modulation of gene transcription, and can function as a recognition and binding site for a family of regulatory proteins, or transcription factors. A TATA box is another conserved nucleotide sequence found in the promoter region of a large number of genes, and is widely believed to be involved in transcription initiation. Indeed, TATA box has been reported to be important in determining accurately the position at which transcription is initiated. In addition, a particular promoter may contain multiple TATA-boxes, in which case each of the TATA boxes may have different strengths; and stronger TATA boxes are reported to increase expression in a more predictable fashion. It has also reported that the sequence and spacing of TATA box elements are important for accurate initiation of transcription (see, e.g., Mogno et al., *Genome Res.* 20: 1391-1397, 2010.)

Other conserved regulatory motifs can be identified using a variety of techniques and methods known in the art. For example, those skilled in the art will recognize that conserved regulatory regions and regulatory motifs can be identified using the PlantCARE web resource, which is a database of plant promoters and their cis-acting regulatory elements, including enhancers and repressors (Lescot et al., *Nucleic Acids Res.*, 30: 325 327, 2002). In PlantCARE database, regulatory elements are represented by positional matrices, consensus sequences and individual sites on particular promoter sequences.

One skilled in the art will further appreciate that conserved regulatory regions and regulatory motifs can be also identified using the PlantProm plant promoter database, which is an annotated, non-redundant collection of proximal promoter sequences for RNA polymerase II with experimentally determined transcription start site(s) (TSS), from various plant species (Shahmuradov et al., 2003 *Nucleic Acids Res.*, 31: 114 117, 2003). It provides DNA sequence of the promoter regions with TSS, taxonomic/promoter type classification of promoters and Nucleotide Frequency Matrices (NFM) for promoter elements: TATA-box, CCAAT-box and TSS-motif.

Additionally, it will be further appreciated by the skilled artisan that conserved regulatory regions and regulatory motifs can also be identified and/or analyzed using the PLACE PLACE (PLAnt Cis-acting regulatory DNA Elements) database, which is a database of nucleotide sequence motifs found in plant cis-acting regulatory DNA elements. See, e.g., Higo et al., *Nucleic Acids Res.*, 27(0:297-300, 1999; and Prestridge, *CABIOS*, 7:203-206, 1991. Approximately 1,340 conserved regulatory motifs can be found in the PLACE database. Depending upon the need for using a specific cis-acting element, the regulatory database can be searched using a web signal scan program that can be found on the World Wide Web at dna.affrc.go.jp/PLACE/signalscan.html. Documents for each motif in the PLACE database contain a motif sequence, a brief definition and description of each motif, and relevant literature with PubMed ID numbers and GenBank accession numbers (Higo et al., 1999, supra). The listed cis-acting regulatory elements in the PLACE database and the cis-acting regulatory elements that are provided in Raumbauts et al. (*Nucleic Acids Res.* 27:295-296 1999) and Higo et al. (1999, supra) can be used with embodiments of the invention. In fact, the PLACE database has been shown to be a useful tool for the identification of cis-acting regulatory elements in algal promoters such as, for example, those responsible for the lighted regulated expression of the phycoerythrin operon in the red alga *Gracilaria lemaneiformis* (Sui et al., *J. Appl. Phycol* 16:167-174, 2004). Accordingly, the cis-regulatory element databases and references above are hereby incorporated by reference in their entireties.

Examples of regulatory elements, which are present in the regulatory regions disclosed herein as determined by the Signal Scan tool of the PLACE database, are disclosed herein at TABLE 1.

Thus, in some embodiments of the present invention, a regulatory region such as any one of the sequences set forth in SEQ ID NO: 1 through SEQ ID NO: 16, or a regulatory region having a nucleotide sequence that deviates from any one of the sequences set forth in SEQ ID NO: 1 through SEQ ID NO: 16, while retaining the ability to direct expression of an operably linked nucleic acid, can contain one or more conserved regulatory motifs, which can be found in the PLACE database. For example, as indicated in the Sequence Listing and TABLE 1, such a regulatory region can contain an AACACOREOSGLUB1 motif having the consensus sequence AACAAAC. See, Wu et al., *Plant J.* 23: 415-421, 2000. Such a regulatory region can also contain an ACG-TOSGLUB 1 motif having the consensus sequence GTACGTG. See, Washida et al., *Plant Mol. Biol.* 40:1-12, 1999; and Wu et al., *Plant J.* 23: 415-421, 2000. Such a regulatory region can contain an AMMORESIJUDCRNIA1 motif having the consensus sequence GGWAGGGT. See, Loppes and Radoux, *Plant Mol. Biol.* 45: 215-227, 2001. Such a regulatory region can also contain a BOXIINTPATPB motif having the consensus sequence ATAGAA. See, Kapoor and Sugiura, *Plant Cell* 11: 1799-1810, 1999. Such a regulatory region can also contain a BOXIIPCCHS motif having the consensus sequence ACGTGGC, See Terzaghi and Cashmore, *Annu. Rev. Plant Physiol. Plant Mol. Biol.* 46:445-474, 1995; and Nakashima et al., *Plant Mol. Biol.* 60: 51-68, 2006. Such a regulatory region can also contain a BOXLCOREDCPAL motif having the consensus sequence ACCWWCC. See, Maeda et al., *Plant Mol. Biol.* 59: 739-752, 2005. Such a regulatory region can also contain a CCA1ATLHCB1 motif having the consensus sequence AAMAATCT. See, Wang et al., *Plant Cell* 9:491-507, 1997. Such a regulatory region can also contain a CELLCYCLESC motif having the consensus sequence CACGAAAA. See, Breeden and Nasmyth, *Cell* 48:389-397, 1987; and Nasmyth et al., *Cell* 62:631-647, 1990. Such a regulatory region can also contain a CIACADIANLELHC motif having the consensus sequence CAANNNNATC. See, Piechulla et al., *Plant Mol. Bio*138:655-662, 1998. Such a regulatory region can also contain a CMSRE1IBSPOA motif having the consensus sequence TGGACGG. See, Morikami et al., *Mol Genet Genomics* 272:690-699, 2005. Such a regulatory region can also contain a DPBFCOREDCDC3 motif having the consensus sequence ACACNNG. See, Kim et al, *Plant* 111: 1237-1251, 1997; Finkelstein and Lynch, *Plant Cell* 12: 599-609, 2000; Lopez-Molina and Chua, *Plant Cell Physiol.* 41: 541-547, 2000. Such a regulatory region can also contain an EECCRCAH1 motif having the consensus sequence GANTTNC. See, Kucho et al., *Plant Physiol.* 133: 783-793 (2003); and Yoshioka et al., *Plant Cell* 16: 1466-1477; 2004. Such a regulatory region can also contain an ERELEE4 motif having the consensus sequence AWTTCAAA. See, Itzhaki et al., Proc. Natl. Acad. Sci. USA 91:8925-8929, 1994; Tapia et al., *Plant Physiol.* 138:2075-2086, 2005; and Rawat et al., *Plant Mol. Biol.* 57: 629-643, 2005. Such a regulatory region can also contain a GBOXLERBCS motif having the consensus sequence MCACGTGGC. See, Giuliano et al., *Proc. Natl. Acad. Sci. USA* 85:7089-7093, 1988; Donald and Cashmore, *EMBO J.* 9:1717-1726, 1990; and Vasil et al., *Plant Cell* 7: 1511-1518, 1995. Such a regulatory region can also contain a GT1CONSENSUS motif having the consensus sequence GRWAAW. See, e.g., Terzaghi and Cashmore, *Annu Rev Plant Physiol. Plant Mol. Biol.* 46:445-474, 1995; and Zhou, *Trends in Plant Science* 4:210-214, 1999. Such a regulatory region can also contain a HDZIP2ATATHB2 motif having the consensus sequence TAATMATTA. See, Ohgishi et al., *Plant J.* 25: 389-398, 2001. Such a regulatory region can also contain an IBOX motif having the consensus sequence GATAAG. See, Giuliano et al., *Proc. Natl. Acad. Sci. USA* 85:7089-7093, 1988; Donald and Cashmore, *EMBO J.* 9:1717-1726, 1990; and Rose et al., *Plant J.* 20: 641-652, 1999. Such a regulatory region can also contain an INRNTPSADB motif having the consensus sequence YTCANTYY. See, Nakamura et al., *Plant J.* 29: 1-10, 2002. Such a regulatory region can also contain a MARARS motif having the consensus sequence WTTTATRTTTW. See, Gasser et al., *Intnatl. Rev. Cyto.* 119:57-96, 1989. Such a regulatory region can also contain a MARTBOX motif having the consensus sequence TTWTWTTWTT. See, Gasser et al.,

*Intnatl Rev Cyto* 119:57-96, 1989. Such a regulatory region can also contain a MYBGAHV motif having the consensus sequence TAACAAA. See, Morita et al., *FEBS Lett* 423: 81-85, 1998; and Gubler et al., *Plant J.* 17:1-9, 1999. Such a regulatory region can also contain a REALPHALGL-HCB21 motif having the consensus sequence AACCAA. See, Degenhardt and Tobin, *Plant Cell* 8: 31-41, 1996. Such a regulatory region can also contain a SORLREP3AT motif having the consensus sequence TGTATATAT. See, Hudson and Quail, *Plant Physiol.* 133: 1605-1616, 2003. Such a regulatory region can also contain a SORLIP5AT motif having the consensus sequence GAGTGAG. See, Hudson and Quail, *Plant Physiol.* 133: 1605-1616, 2003; and Jiao et al., *Plant Cell* 17: 3239-3256, 2005. Such a regulatory region can also contain a SP8BFIBSP8BIB motif having the consensus sequence TACTATT. See, Ishiguro and Nakamura, *Plant Mol. Biol.* 18:97-108, 1992; Ishiguro and Nakamura, *Mol. Gen. Genet,* 244: 563-571, 1994. Such a regulatory region can also contain a SV4000REENHAN motif having the consensus sequence GTGGWWHG. See, Weiher et al., *Science* 219:626-631, 1983; Donald and Cashmore, *EMBO J.* 9:1717-1726, 1990; and Green et al., *EMBO J.* 6:2543-2549, 1987. Such a regulatory region can also contain a TATABOX2 motif having the consensus sequence TATAAAT. See, Grace et al., *J. Biol. Chem.* 279:8102-8110 2004. Such a regulatory region can also contain a TATA-BOX3 motif having the consensus sequence TATAAAT. Such a regulatory region can also contain a TATABOX4 motif having the consensus sequence TATATAA. See, Grace et al., 2004, supra. Such a regulatory region can also contain a TATABOX5 motif having the consensus sequence TTATTT. See, Tjaden et al., *Plant Physiol.* 108:1109-1117, 1995. Such a regulatory region can also contain a TBOX-ATGAPB motif having the consensus sequence ACTTTG. See, Chan et al., *Plant Mal. Biol.* 46: 131-141, 2001. Such a regulatory region can also contain a VSF1PVGRP18 motif having the consensus sequence GCTCCGTTG. See, Ringli and Keller, *Plant Mol. Biol.* 37:977-988, 1998; and Torres-Schumann et al., *Plant J.* 9:283-296, 1996. Such a regulatory region can also contain a WBBOXPCWRKY1 motif having the consensus sequence TTTGACY. See, Eulgem et al., *Trends Plant Sci.* 5: 199-206, 2000. Such a regulatory region can also contain a WUSATAG motif having the consensus sequence TTAATGG. See, Kamiya et al., *Plant J.* 35: 429-441, 2003. Such a regulatory region can also contain a ZDNAFORMINGATCAB1 motif having the consensus sequence ATACGTGT. See, Yadav et al., *Plant Cell* 17: 1953-1966, 2005.

TABLE 1

Exemplary regulatory motifs present in the regulatory regions of the present invention.

| Regulatory region | Regulatory element | Location | Strand | Consensus sequence |
|---|---|---|---|---|
| EMRE1EUKS708914 | CIACADIANLELHC | 34 | (−) | CAANNNNATC |
| (SEQ ID NO: 1) | DPBFCOREDCDC3 | 434 | (+) | ACACNNG |
| | DPBFCOREDCDC3 | 736 | (+) | ACACNNG |
| | DPBFCOREDCDC3 | 5 | (−) | ACACNNG |
| | EECCRCAH1 | 545 | (+) | GANTTNC |
| | EECCRCAH1 | 699 | (+) | GANTTNC |
| | EECCRCAH1 | 795 | (−) | GANTTNC |
| | GT1CONSENSUS | 242 | (+) | GRWAAW |
| | GT1CONSENSUS | 351 | (+) | GRWAAW |
| | GT1CONSENSUS | 352 | (+) | GRWAAW |
| | GT1CONSENSUS | 766 | (+) | GRWAAW |
| | GT1CONSENSUS | 927 | (+) | GRWAAW |
| | GT1CONSENSUS | 546 | (−) | GRWAAW |
| | REALPHALGLHCB21 | 371 | (−) | AACCAA |
| | SV40COREENHAN | 895 | (−) | GTGGWWHG |
| | TATABOX2 | 97 | (−) | TATAAAT |
| | TATABOX5 | 515 | (−) | TTATTT |
| | VSF1PVGRP18 | 675 | (−) | GCTCCGTTG |
| EMRE1EUKS708913 | ACGTOSGLUB1 | 37 | (−) | GTACGTG |
| (SEQ ID NO: 2) | BOXIINTPATPB | 516 | (+) | ATAGAA |
| | BOXIINTPATPB | 29 | (−) | ATAGAA |
| | BOXLCOREDCPAL | 366 | (−) | ACCWWCC |
| | CMSRE1IBSPOA | 759 | (+) | TGGACGG |
| | DPBFCOREDCDC3 | 247 | (−) | ACACNNG |
| | DPBFCOREDCDC3 | 584 | (−) | ACACNNG |
| | GT1CONSENSUS | 620 | (−) | GRWAAW |
| | GT1CONSENSUS | 964 | (−) | GRWAAW |
| | SORLIP5AT | 718 | (+) | GAGTGAG |
| | SV40COREENHAN | 837 | (+) | GTGGWWHG |
| | TBOXATGAPB | 68 | (−) | ACTTTG |
| EMRE1EUKS708905 | BOXIINTPATPB | 531 | (−) | ATAGAA |
| (SEQ ID NO: 3) | BOXIINTPATPB | 627 | (−) | ATAGAA |
| | BOXIINTPATPB | 909 | (−) | ATAGAA |
| | BOXIIPCCHS | 26 | (−) | ACGTGGC |
| | CCA1ATLHCB1 | 413 | (+) | AAMAATCT |
| | CIACADIANLELHC | 826 | (−) | CAANNNNATC |
| | DPBFCOREDCDC3 | 692 | (+) | ACACNNG |
| | DPBFCOREDCDC3 | 28 | (−) | ACACNNG |
| | DPBFCOREDCDC3 | 811 | (−) | ACACNNG |
| | EECCRCAH1 | 687 | (+) | GANTTNC |
| | EECCRCAH1 | 496 | (−) | GANTTNC |

TABLE 1-continued

Exemplary regulatory motifs present in the regulatory regions of the present invention.

| Regulatory region | Regulatory element | Location | Strand | Consensus sequence |
|---|---|---|---|---|
| | GBOXLERBCS | 26 | (-) | MCACGTGGC |
| | GT1CONSENSUS | 836 | (+) | GRWAAW |
| | GT1CONSENSUS | 94 | (-) | GRWAAW |
| | GT1CONSENSUS | 242 | (-) | GRWAAW |
| | GT1CONSENSUS | 475 | (-) | GRWAAW |
| | GT1CONSENSUS | 95 | (-) | GRWAAW |
| | GT1CONSENSUS | 200 | (-) | GRWAAW |
| | REALPHALGLHCB21 | 786 | (+) | AACCAA |
| | REALPHALGLHCB21 | 213 | (-) | AACCAA |
| | SV40COREENHAN | 563 | (-) | GTGGWWHG |
| | TATABOX5 | 950 | (+) | TTATTT |
| | TBOXATGAPB | 195 | (-) | ACTTTG |
| EMRE1EUKS708903 (SEQ ID NO: 4) | ABRELATERD1 | 400 | (-) | ACGTG |
| | BOXLCOREDCPAL | 686 | (+) | ACCWWCC |
| | DPBFCOREDCDC3 | 630 | (-) | ACACNNG |
| | GT1CONSENSUS | 295 | (+) | GRWAAW |
| | GT1CONSENSUS | 827 | (+) | GRWAAW |
| | GT1CONSENSUS | 741 | (-) | GRWAAW |
| | GT1CONSENSUS | 282 | (-) | GRWAAW |
| | GT1CONSENSUS | 911 | (-) | GRWAAW |
| | GT1CONSENSUS | 933 | (-) | GRWAAW |
| | REALPHALGLHCB21 | 685 | (+) | AACCAA |
| | TATABOX2 | 801 | (+) | TATAAAT |
| | TATABOX5 | 662 | (+) | TTATTT |
| | TATABOX5 | 739 | (+) | TTATTT |
| EMRE1EUKS708920 (SEQ ID NO: 5) | AMMORESIIUDCRNIA1 | 89 | (-) | GGWAGGGT |
| | CELLCYCLESC | 203 | (+) | CACGAAAA |
| | CMSRE1IBSPOA | 257 | (+) | TGGACGG |
| | DPBFCOREDCDC3 | 296 | (+) | ACACNNG |
| | DPBFCOREDCDC3 | 384 | (+) | ACACNNG |
| | DPBFCOREDCDC3 | 165 | (-) | ACACNNG |
| | DPBFCOREDCDC3 | 215 | (-) | ACACNNG |
| | GT1CONSENSUS | 206 | (+) | GRWAAW |
| | REALPHALGLHCB21 | 421 | (-) | AACCAA |
| | SV40COREENHAN | 96 | (-) | GTGGWWHG |
| | SV40COREENHAN | 369 | (-) | GTGGWWHG |
| | WBBOXPCWRKY1 | 149 | (+) | TTTGACY |
| EMRE1EUKS708902 (SEQ ID NO: 6) | BOXIINTPATPB | 22 | (+) | ATAGAA |
| | BOXIIPCCHS | 578 | (+) | ACGTGGC |
| | CIACADIANLELHC | 607 | (-) | CAANNNNATC |
| | CMSRE1IBSPOA | 317 | (+) | TGGACGG |
| | DPBFCOREDCDC3 | 226 | (+) | ACACNNG |
| | DPBFCOREDCDC3 | 472 | (+) | ACACNNG |
| | DPBFCOREDCDC3 | 895 | (+) | ACACNNG |
| | DPBFCOREDCDC3 | 227 | (-) | ACACNNG |
| | EECCRCAH1 | 562 | (-) | GANTTNC |
| | EECCRCAH1 | 920 | (-) | GANTTNC |
| | GT1CONSENSUS | 155 | (+) | GRWAAW |
| | GT1CONSENSUS | 156 | (+) | GRWAAW |
| | GT1CONSENSUS | 562 | (+) | GRWAAW |
| | GT1CONSENSUS | 750 | (+) | GRWAAW |
| | GT1CONSENSUS | 14 | (-) | GRWAAW |
| | REALPHALGLHCB21 | 369 | (+) | AACCAA |
| | SORLIP5AT | 663 | (+) | GAGTGAG |
| | TATABOX2 | 951 | (-) | TATAAAT |
| | ITBOXATGAPB | 493 | (+) | ACTTTG |
| EMRE1EUKG11871 (SEQ ID NO: 7) | AACACOREOSGLUB1 | 274 | (+) | AACAAAC |
| | GT1CONSENSUS | 29 | (+) | GRWAAW |
| | GT1CONSENSUS | 66 | (+) | GRWAAW |
| | GT1CONSENSUS | 67 | (+) | GRWAAW |
| | GT1CONSENSUS | 208 | (+) | GRWAAW |
| | GT1CONSENSUS | 224 | (+) | GRWAAW |
| | GT1CONSENSUS | 56 | (-) | GRWAAW |
| | HDZIP2ATATHB2 | 40 | (+) | TAATMATTA |
| | MARTBOX | 30 | (+) | TTWTWTTWTT |
| | MARTBOX | 33 | (-) | TTWTWTTWTT |
| | TATABOX5 | 202 | (+) | TTATTT |
| | TATABOX5 | 37 | (-) | TTATTT |
| | TATABOX5 | 252 | (-) | TTATTT |

TABLE 1-continued

Exemplary regulatory motifs present in the regulatory regions of the present invention.

| Regulatory region | Regulatory element | Location | Strand | Consensus sequence |
|---|---|---|---|---|
| EMRE1EUKG11849 (SEQ ID NO: 8) | BOXIINTPATPB | 55 | (+) | ATAGAA |
| | CCA1ATLHCB1 | 59 | (+) | AAMAATCT |
| | GT1CONSENSUS | 58 | (+) | GRWAAW |
| | GT1CONSENSUS | 97 | (+) | GRWAAW |
| | GT1CONSENSUS | 132 | (−) | GRWAAW |
| | GT1CONSENSUS | 81 | (−) | GRWAAW |
| | MYBGAHV | 148 | (−) | TAACAAA |
| | REALPHALGLHCB21 | 26 | (−) | AACCAA |
| | REALPHALGLHCB21 | 77 | (−) | AACCAA |
| | TATABOX2 | 87 | (+) | TATAAAT |
| EMRE1EUKG11833 (SQ ID NO: 9) | CIACADIANLELHC | 34 | (−) | CAANNNNATC |
| | EECCRCAH1 | 26 | (+) | GANTTNC |
| | GT1CONSENSUS | 43 | (+) | GRWAAW |
| | GT1CONSENSUS | 50 | (−) | GRWAAW |
| | HDZIP2ATATHB2 | 45 | (−) | TAATMATTA |
| | MARTBOX | 92 | (+) | TTWTWTTWTT |
| | SORLREP3AT | 179 | (−) | TGTATATAT |
| | TATABOX5 | 92 | (+) | TTATTT |
| EMRE1EUKG11868 (SEQ ID NO: 10) | ACGTOSGLUB1 | 28 | (+) | GTACGTG |
| | GT1CONSENSUS | 167 | (+) | GRWAAW |
| | MARTBOX | 190 | (−) | TTWTWTTWTT |
| | TATABOX5 | 189 | (−) | TTATTT |
| EMRE1EUKG11888 (SEQ ID NO: 11) | BOXIINTPATPB | 49 | (−) | ATAGAA |
| | EECCRCAH1 | 104 | (+) | GANTTNC |
| | GT1CONSENSUS | 15 | (+) | GRWAAW |
| | GT1CONSENSUS | 105 | (−) | GRWAAW |
| | MARTBOX | 16 | (−) | TTWTWTTWTT |
| | MARTBOX | 21 | (−) | TTWTWTTWTT |
| | REALPHALGLHCB21 | 63 | (+) | AACCAA |
| | TATABOX2 | 26 | (+) | TATAAAT |
| | TATABOX2 | 124 | (−) | TATAAAT |
| | TATABOX3 | 33 | (+) | TATTAAT |
| | TATABOX4 | 127 | (+) | TATATAA |
| | TATABOX4 | 126 | (−) | TATATAA |
| | TATABOX4 | 152 | (−) | TATATAA |
| | TATABOX5 | 20 | (−) | TTATTT |
| EMRE1EUKG11818 (SEQ ID NO: 12) | SP8BFIBSP8BIB | 175 | (+) | TACTATT |
| | TATABOX2 | 75 | (+) | TATAAAT |
| | TATABOX5 | 156 | (+) | TTATTT |
| | TATABOX5 | 160 | (+) | TTATTT |
| | TATABOX5 | 164 | (+) | TTATTT |
| | TATABOX5 | 93 | (−) | TTATTT |
| | TATABOX5 | 183 | (−) | TTATTT |
| | TBOXATGAPB | 148 | (−) | ACTTTG |
| | WBBOXPCWRKY1 | 145 | (−) | TTTGACY |
| EMRE1EUKG11812 (SEQ ID NO: 13) | GT1CONSENSUS | 56 | (+) | GRWAAW |
| | MARTBOX | 191 | (−) | TTWTWTTWTT |
| | TATABOX5 | 190 | (−) | TTATTT |
| | TATABOX5 | 195 | (−) | TTATTT |
| N. gaditana AHAS (SEQ ID NO: 14) | AACACOREOSGLUB1 | 249 | (−) | AACAAAC |
| | CCA1ATLHCB1 | 36 | (−) | AAMAATCT |
| | CCA1ATLHCB1 | 188 | (−) | AAMAATCT |
| | CIACADIANLELHC | 273 | (−) | CAANNNNATC |
| | EECCRCAH1 | 50 | (+) | GANTTNC |
| | EECCRCAH1 | 273 | (+) | GANTTNC |
| | EECCRCAH1 | 367 | (−) | GANTTNC |
| | GT1CONSENSUS | 355 | (+) | GRWAAW |
| | GT1CONSENSUS | 488 | (+) | GRWAAW |
| | GT1CONSENSUS | 51 | (−) | GRWAAW |
| | GT1CONSENSUS | 64 | (−) | GRWAAW |
| | GT1CONSENSUS | 274 | (−) | GRWAAW |
| | GT1CONSENSUS | 42 | (−) | GRWAAW |
| | GT1CONSENSUS | 93 | (−) | GRWAAW |
| | GT1CONSENSUS | 134 | (−) | GRWAAW |
| | GT1CONSENSUS | 175 | (−) | GRWAAW |
| | GT1CONSENSUS | 223 | (−) | GRWAAW |
| | GT1CONSENSUS | 264 | (−) | GRWAAW |
| | SP8BFIBSP8BIB | 155 | (−) | TACTATT |

TABLE 1-continued

Exemplary regulatory motifs present in the regulatory regions of the present invention.

| Regulatory region | Regulatory element | Location | Strand | Consensus sequence |
|---|---|---|---|---|
| | SP8BF1BSP8BIB | 325 | (−) | TACTATT |
| | TATABOX5 | 89 | (+) | TTATTT |
| | TATABOX5 | 240 | (+) | TTATTT |
| | TATABOX5 | 300 | (−) | TTATTT |
| | TATABOX5 | 428 | (−) | TTATTT |
| | TBOXATGAPB | 440 | (−) | ACTTTG |
| N. salina AHAS (SEQ ID NO: 15) | AACACOREOSGLUB1 | 229 | (−) | AACAAAC |
| | CCA1ATLHCB1 | 168 | (−) | AAMAATCT |
| | CIACADIANLELHC | 253 | (−) | CAANNNNATC |
| | EECCRCAH1 | 30 | (+) | GANTTNC |
| | EECCRCAH1 | 253 | (+) | GANTTNC |
| | EECCRCAH1 | 347 | (−) | GANTTNC |
| | GT1CONSENSUS | 335 | (+) | GRWAAW |
| | GT1CONSENSUS | 468 | (+) | GRWAAW |
| | GT1CONSENSUS | 31 | (−) | GRWAAW |
| | GT1CONSENSUS | 44 | (−) | GRWAAW |
| | GT1CONSENSUS | 123 | (−) | GRWAAW |
| | GT1CONSENSUS | 254 | (−) | GRWAAW |
| | GT1CONSENSUS | 22 | (−) | GRWAAW |
| | GT1CONSENSUS | 73 | (−) | GRWAAW |
| | GT1CONSENSUS | 114 | (−) | GRWAAW |
| | GT1CONSENSUS | 155 | (−) | GRWAAW |
| | GT1CONSENSUS | 203 | (−) | GRWAAW |
| | GT1CONSENSUS | 244 | (−) | GRWAAW |
| | SP8BFIBSP8BIB | 135 | (−) | TACTATT |
| | SP8BFIBSP8BIB | 305 | (−) | TACTATT |
| | TATABOX5 | 220 | (+) | TTATTT |
| | TATABOX5 | 280 | (−) | TTATTT |
| | TATABOX5 | 408 | (−) | TTATTT |
| | TBOXATGAPB | 145 | (−) | ACTTTG |
| | TBOXATGAPB | 420 | (−) | ACTTTG |
| | CIACADIANLELHC | 3 | (−) | CAANNNNATC |
| N. oculata AHAS (SEQ ID NO: 16) | EECCRCAH1 | 3 | (+) | GANTTNC |
| | EECCRCAH1 | 97 | (−) | GANTTNC |
| | EECCRCAHI | 194 | (−) | GANTTNC |
| | GT1CONSENSUS | 85 | (+) | GRWAAW |
| | GT1CONSENSUS | 230 | (+) | GRWAAW |
| | GT1CONSENSUS | 4 | (−) | GRWAAW |
| | MARARS | 175 | (+) | WTTTATRTTTW |
| | SP8BFIBSP8BIB | 55 | (−) | TACTATT |
| | TATABOX5 | 30 | (−) | TTATTT |
| | TATABOX5 | 158 | (−) | TTATTT |
| | TATABOX5 | 162 | (−) | TTATTT |
| | TATABOX5 | 233 | (−) | TTATTT |

In one embodiment, the promoters of the present invention can include a nucleic acid sequence which has one or more nucleotides being substituted, deleted, inserted, or added relative to the nucleic acid sequence of a referenced promoter molecule, and which exhibits promoter activity. As such, any of the nucleic acid molecules described herein may comprise nucleic acid sequences comprising promoters. Promoters of the present invention can include between about 0.01 Kb and about 50 Kb, more preferably between about 0.1 Kb and about 25 Kb, even more preferably between about 0.5 Kb and about 10 Kb, and most preferably between about 1 Kb and about 10 Kb, about 2 Kb and about 7 Kb, about 3 Kb and about 6 Kb, about 2 Kb and about 4 Kb, about 2 Kb and about 5 Kb, about 0.5 Kb and about 5 Kb, about 0.5 Kb and about 3 Kb, or about 1 Kb and about 2 Kb, upstream of the trinucleotide sequence located at the translational start site of a protein coding region.

The regulatory polynucleotide sequences of the present invention can be modified to provide for a range of expression levels of the isolated nucleotide sequence. Less than the entire promoter region can be utilized and the ability to drive gene expression. It is widely recognized that expression levels of mRNA can be modulated with specific deletions of portions of a promoter sequence. Thus, a promoter can be modified to be a weaker or stronger promoter as compared to the unmodified reference promoter. Generally, by "weak promoter" is intended a promoter that drives expression of a coding sequence at a low level. By "low level" is intended levels of about 1/10,000 transcripts to about 1/100,000 transcripts to about 1/500,000 transcripts per cell. Conversely, a strong promoter drives expression of a coding sequence at a high level or at about 1/10 transcripts to about 1/100 transcripts to about 1/1,000 transcripts per cell. Generally, at least about 20 nucleotides of an isolated promoter sequence will be used to drive expression of an operably linked transcribable polynucleotide sequence.

Promoter Activity

A number of techniques and methods that are well known to those skilled in the art can be used for the identification and characterization of promoter activity. Further, a polynucleotide molecule having promoter activity can additionally be evaluated by testing the ability of the polynucleotide molecule to drive expression in a transgene in a transgenic cells, e.g., algal cell and plant cell.

As used herein, the term "expression" or "gene expression" refers to the process of converting genetic information of a polynucleotide into RNA through transcription. Gene expression may be described as related to temporal, spatial, developmental, or morphological qualities as well as quantitative or qualitative indications. The transcription product, i.e. the RNA molecule, may be translated to produce a protein molecule, or may provide a structural ribosomal RNA molecule, or may provide an antisense or other regulatory RNA molecule.

As used herein, an "expression pattern" is any pattern of differential gene expression. In a preferred embodiment, an expression pattern is selected from the group consisting of developmental, spatial, temporal, organelle, tissue, stress, environmental, nutritional, physiological, pathological, cell cycle, and chemically responsive expression patterns.

As used herein, an "enhanced expression pattern" refers to an elevated, increased or high expression level of a particular gene or a particular operably linked nucleic acid sequence in a transgenic cell as compared to the expression level of the same gene found in an untransformed cell, i.e. where the genome has not been altered by the presence of a recombinant nucleic acid. When used in reference to an exogenous gene, the term "enhanced expression pattern" is any expression pattern for which an operably linked nucleic acid sequence is expressed at a level greater than 0.01%; more preferably greater than 0.05, 0.1, 0.25, 0.5, 0.75, 1, 2, 3, 4, 5, 6, 7, 8, 9, 10, 11, 12, 13, 14, 15, 16, 17, 18, 19, or 20% (w/w) of the total cellular RNA or protein.

The activity or strength of a promoter may be measured in terms of the amount of mRNA or protein accumulation it specifically produces, relative to the total amount of mRNA or protein, by using well known techniques such as quantitative RT-PCR, Northern blot analysis, Western blot analysis, fluorescent reporter genes, and the like. See, for example, Sambrook et al. (1989, supra). In a preferred embodiment, the promoters of the in present invention expresses an operably linked transcribable polynucleotide molecule at a level greater than 0.01%; more preferably greater than 0.05, 0.1, 0.25, 0.5, 0.75, 1, 2, 3, 4, 5, 6, 7, 8, 9, 10, 11, 12, 13, 14, 15, 16, 17, 18, 19, or 20% (w/w) of the total cellular RNA or protein.

Alternatively, the activity or strength of a promoter may be expressed relative to a well-characterized promoter (for which transcriptional activity was previously assessed). For example, a less-characterized promoter may be operably linked to a reporter sequence (e.g., green fluorescence protein, GFP) and introduced into a specific cell type. A well-characterized promoter (e.g. a SV40 promoter from simian virus or a 35S promoter from cauliflower mosaic virus) is similarly prepared and introduced into the same cellular context. Transcriptional activity of the unknown promoter is determined by comparing the amount of reporter expression, relative to the well characterized promoter. In one embodiment, the activity of the present promoter is as strong as the 35S promoter when compared in the same cellular context. The cellular context is preferably an algal cell, a bacterial cell, a fungal cell, or a plant cell; and more preferably is a microalgal cell or a microfungal cell; and most preferably is a *Nannochloropsis* cell.

Untranslated Regions

The regulatory elements in accordance with the present invention include untranslated regions (UTRs). A "UTR", as used herein, refers to any contiguous series of nucleotide bases that is transcribed, but is not translated. Examples of UTRs include but are not limited to polyadenylation signals, termination sequences, sequences located between the transcriptional start site and the first exon (i.e., leader or 5'-UTR), and sequences located between the last exon and the end of the mRNA (3'-UTR). UTRs are known to play crucial roles in the post-transcriptional regulation of gene expression, including modulation of the transport of mRNAs out of the nucleus and of translation efficiency, subcellular localization and stability. For example, while 5'-UTR is reported to function to regulate both mRNA stability as well as translation, 3'-UTR appears to influence mRNA processing and stability.

As used herein, the term "leader", which is sometimes defined as 5'-untranslated region (5'-UTR), generally refers to the portion of the DNA between the transcription start site (TSS, or the cap site) and the coding sequence start site. As such, the 5'-UTR region of a gene is transcribed into mRNA, becoming the 5' end of the message, but which does not contain protein coding sequence. While this region itself is not translated, it may comprise sequence elements which alter the translation efficiency of the mRNA, or which affect the stability of the mRNA. Leaders may be isolated based on the nucleotide sequence from the untranslated 5' region (5' UTR) of a genomic copy of a gene. Alternately, leaders may be synthetically produced or manipulated non-coding DNA elements. As such, leaders need not be of naturally-occurring sequences. In addition, it will be understood that such leaders can be native or non-native, and thus need not be derived from the target host cell or host organism.

Regulation of gene expression by UTRs is mediated in several ways. Nucleotide patterns or motifs located in 5'-UTRs and 3'-UTRs can interact with specific RNA-binding proteins. Unlike DNA-mediated regulatory signals, however, whose activity is essentially mediated by their primary structure, the biological activity of regulatory motifs at the RNA level relies on a combination of primary and secondary structure. Interactions between sequence elements located in the UTRs and specific complementary RNAs have also been shown to play key regulatory roles. Finally, there are examples of repetitive elements that are important for regulation at the RNA level, affecting translation efficiency.

For example, non-translated 5' leader polynucleotide molecules derived from heat shock protein genes have been demonstrated to enhance gene expression in plants and animals (see, e.g., U.S. Pat. Nos. 5,659,122; 5,362,865; 7,351,818). In microalgae, such as *Chlamydomonas reinhardtii*, a number of regulatory elements have been identified in either the 5'- or 3'-untranslated regions of plastid mRNAs that can significantly boost mRNA levels and support high levels of heterologous protein accumulation in algal cells (Rasala et al., *Plant Biotechnol. J.* 9(6):674-683, 2011; Barnes et al., *Mol. Genet. Genomics,* 274(6):625-36, 2005).

Translational enhancers may also be incorporated as part of a nucleic acid vector in accordance with the present invention. Thus the vector may preferably contain one or more 5' cis-acting sequences and leader sequences which serve to enhance expression of the nucleic acid sequence. Such enhancer sequences may be desirable to increase or alter the translational efficiency of the resultant mRNA. Examples of other non-coding regulatory elements that are 5' nucleic acid leader sequences include dSSU 5', PetHSP70 5', and GmHSP17.9 5' (see, e.g., U.S. Pat. No. 7,790,958).

Introns

In one embodiment, the regulatory polynucleotide molecules according to the present invention include introns. As used herein, the term "intron" refers to a non-coding polynucleotide molecule. Introns may be isolated from the intervening (non-coding) sequence of a genomic copy of a gene and may be defined generally as a region spliced out during mRNA processing prior to translation. Alternately, introns may be synthetically produced or manipulated non-coding DNA elements. As such, introns need not be of naturally-occurring sequences. In addition, it will be understood that such introns can be native or non-native, and thus need not be derived from the target host cell or host organism.

Introns may affect the expression of an operably linked polynucleotide sequence transcriptionally or post-transcriptionally. Introns may themselves contain sub-elements such as cis-acting elements or enhancer domains that boost or weaken the transcription of operably linked transcribable polynucleotide molecules. Introns may also affect transgenes through post-transcriptional events such as nuclear export or transcript stability. The expression of a transgene often benefit from the proper use of introns. As such, an intron can be used as a regulatory element for modulating expression of an operably linked gene or genes.

In another embodiment, the transcribable polynucleotide molecule sequence in the nucleic acid constructs according to the present invention may comprise introns. The introns may be heterologous with respect to the transcribable polynucleotide molecule sequence. Examples of other non-coding regulatory element introns include the corn actin intron and the corn HSP70 intron (see, e.g., U.S. Pat. No. 5,859, 347), rice polyubiquitin introns (see, e.g., Sivamani et al., *Plant Mol. Biol.* 60(2):225-39, 2006), and maize ubiquitin introns (see, e.g., Bourdon et al., *EMBO reports* 2, 5, 394-398, 2001). Another well-documented example of non-coding regulatory elements is the first intron of the microalga *Chlamydomonas reinhardtii* RBCS2 gene, which has been inserted into the coding region of several foreign genes to promote stable high-level expression of the foreign genes in *Chlamydomonas* sp. In fact, the introduction of the RBCS2 intron into the coding sequence of the ble selectable marker gene (Lumbreras et al., *Plant J.* 14, 4:441-447, 1998) has drastically improved the expression of this marker, making it one of the very best selectable markers so far for algal transformation systems.

Fragments and Chimeric Regulatory Molecules

In one embodiment, the present invention provides regulatory elements comprising a polynucleotide sequence substantially homologous to a polynucleotide sequence selected from the group consisting of SEQ ID NOs: 1-16, or any fragments thereof that are capable of regulating transcription of operably linked transcribable polynucleotide molecules, e.g., having promoter activity. The term "fragment" or "fragment thereof", as used herein in reference to a polynucleotide molecule, is intended to refer to a finite polynucleotide sequence length that comprises at least 25, at least 50, at least 75, at least 85, or at least 95 contiguous nucleotide bases wherein its complete sequence in entirety is identical to a contiguous component of the referenced polynucleotide molecule. Specifically, a fragment of a polynucleotide sequence provided herein is defined as comprising at least about 20, 30, 40, 50, 75, 100, 125, 150, 200, 250, 300, 350, 400, 450, 500, 600, 750, 900, 1000, or more contiguous nucleotides of any of the polynucleotide sequences described herein, including, for example, SEQ ID NOs: 1-16.

As used herein, a "functional fragment" is a truncated regulatory polynucleotide molecule formed by one or more deletions from a larger regulatory polynucleotide molecule. For example, the 5' portion of a promoter up to the TATA box near the transcription start site sometimes can be deleted without abolishing promoter activity, as described by Opsahl-Sorteberg et al. (*Gene* 341:49-58, 2004). Such fragments can retain promoter activity, particularly the ability to modulate gene expression. Functional fragments can be obtained by use of restriction enzymes to cleave the naturally occurring regulatory polynucleotide sequences disclosed herein; by synthesizing a nucleotide sequence from the naturally occurring DNA sequence; or can be obtained through the use of any of a variety of PCR-based techniques. See, e.g., Erlich, ed., *PCR Technology* (Stockton Press, New York, 1989); Mullis, et al., (*Methods Enzymol.* 155:335-350, 1987); and Gibson DNA assembly technology (*Nature Methods,* 7,901-903, 2010; GIBSON ASSEMBLY™).

For example, a routine way to remove part of a DNA sequence is to use an exonuclease in combination with DNA amplification to produce unidirectional nested deletions of double stranded DNA clones. A commercial kit for this purpose is sold under the trade name "Deletion Kit for Kilo-Sequencing" (Clontech Laboratories Inc., Mountain View, Calif.). Briefly, this procedure entails incubating exonuclease III with DNA to progressively remove nucleotides in the 3' to 5' direction at 5' overhangs, blunt ends or nicks in the DNA template. However, exonuclease III is generally less active in removing nucleotides at 3', 4-base overhangs. Aliquots removed at timed intervals from an Exonuclease III reaction of a clone produces serial unidirectional nested deletions, which then can be treated with Mung Bean Nuclease/buffer cocktail which stops the action of the exonuclease and simultaneously removes the resulting 5'-overhang bases on the complementary strand. The ends of the deleted fragments are blunt-ended using Klenow fragment, and are circularized by ligation using the Ligation cocktails included. The DNA is then used to transform competent bacterial cells.

As described above, promoter activity of fragments, including functional fragments of the regulatory polynucleotide molecules disclosed herein can be tested and/or measured by a variety of well-known techniques such as, for example, quantitative RT-PCR, Northern blot analysis, Western blot analysis, reporter activity measurements when using transcriptional fusions, and the like. See, for example, Sambrook et al., (1989, supra).

In one embodiment, chimeric regulatory molecules which combine regulatory elements from different regulatory polynucleotide molecules disclosed herein are also encompassed by the present invention. As used herein, the term "chimeric" refers to the product of the fusion of portions of two or more different polynucleotide molecules. As such a chimeric regulatory molecule refers to a gene expression regulatory element produced through the manipulation of known elements or other polynucleotide molecules. Novel chimeric regulatory elements can be designed or engineered by a number of methods. In one embodiment of the present invention, a chimeric promoter may be produced by fusing a regulatory element from a first promoter to a second promoter. The resultant chimeric promoter may have novel expression properties relative to the first or second promoters. One skilled in the art will also appreciate that novel chimeric promoters can be constructed such that the regulatory element from a first promoter is fused at the 5' end, at the 3' end, or at any position internal to the second promoter. In addition, the location of the regulatory element fusion relative to the second promoter may cause the resultant chimeric promoter to have novel expression properties relative to a fusion made at a different location. Indeed, cis-regulatory elements can be mixed and matched (programmed) with outcomes on expression that can be predictable based on the rules of simple protein-protein and protein-DNA interactions, as recently described in, for example, Mogno et al., *Genome Res.* 20: 1391-1397, 2010.

In another embodiment of the present invention, chimeric molecules may combine regulatory elements that can confer or modulate gene expression from one or more promoters, by fusing a heterologous regulatory element from a first promoter to a second promoter with its own partial or complete regulatory elements. Novel combinations comprising fragments of these polynucleotide molecules and at least one other regulatory element or fragment can be constructed and tested in vitro and/or in vivo and are considered to be within the scope of this invention. Thus, the design, construction, and use of chimeric regulatory elements are disclosed herein in one aspect of the present invention.

Transcribable Polynucleotide Molecules

A regulatory element of the present invention may be operably linked to a transcribable polynucleotide sequence that is heterologous with respect to the regulatory element. As described in detail above, the term "heterologous" refers to the relationship between two or more sequences that are derived from different sources. As such, "heterologous sequences" are those that are not operably linked or are not contiguous to each other in nature. Thus, a promoter is heterologous with respect to a transcribable polynucleotide sequence if such a combination is not normally found in nature. In addition, a particular sequence may be "heterologous" with respect to a cell or organism into which it is inserted (i.e. does not naturally occur in that particular cell or organism).

Exemplary transcribable polynucleotide molecules for incorporation into nucleic acid constructs of the present invention include, for example, polynucleotide molecules or genes from a species other than the target species or genes that originate with or are present in the same species, but are incorporated into recipient cells by genetic engineering methods rather than classical reproduction or breeding techniques. The type of transcribable polynucleotide molecule can include but is not limited to a polynucleotide molecule that is already present in the host cell, a polynucleotide molecule from another host cell, a polynucleotide molecule from a different organism, or a polynucleotide molecule generated externally, such as a polynucleotide molecule containing an antisense message of a gene, or a polynucleotide molecule encoding an artificial, synthetic, or otherwise modified version of a transgene.

The transcribable polynucleotide molecule may generally be any nucleic acid sequence for which an increased level of transcription is desired. Alternatively, the regulatory element and transcribable polynucleotide sequence may be designed to down-regulate a specific nucleic acid sequence. This down-regulation typically can be accomplished by using one or more of a variety of gene suppression technologies well known to those skilled in the art, such as antisense technology, co-suppression technology, or interfering RNA technology. Briefly, antisense inhibition refers to the production of antisense RNA transcript capable of suppressing the expression of a target gene or protein product. An antisense effect can be accomplished by linking a promoter to a transcribable polynucleotide sequence that is oriented in the antisense direction. As the antisense nucleic acid sequence is transcribed, it hybridizes to and sequesters a complimentary nucleic acid sequence inside the cell (i.e., target nucleic acid sequence). This duplex RNA molecule cannot be translated into a protein by the cell's translational machinery, thereby prevents or inhibits the expression of the target nucleic acid sequence. On the other hand, co-suppression refers to the production of sense RNA transcript capable of suppressing the expression of identical or substantially similar foreign or endogenous genes (see, e.g., U.S. Pat. No. 5,231,020). More recent work has described the use of "hairpin" structures that incorporate all, or part, of an mRNA encoding sequence in a complementary orientation that results in a potential "stem-loop" structure of the expressed RNA, thereby increase the frequency and efficacy of co-suppression in the transgenic cell. Additionally, small interfering RNA (siRNA) are small pieces of double-stranded (ds) RNA, usually about 21 nucleotides long, typically with 3' overhangs at each end that can be used to "interfere" with the translation of proteins by binding to and promoting the degradation of messenger RNA (mRNA) at specific sequences. In doing so, they prevent or inhibit the production of specific proteins based on the nucleotide sequences of their corresponding mRNA. The process is generally called RNA interference (RNAi), and may also be referred to as siRNA silencing or siRNA knockdown.

In one embodiment, it is contemplated by the Applicants herein that a regulatory element of the present invention may also be operably linked to a modified transcribable polynucleotide molecule that is heterologous with respect to the promoter. The transcribable polynucleotide molecule may be modified to provide various desirable features. For example, a transcribable polynucleotide molecule may be modified to increase the content of essential amino adds, enhance translation of the amino acid sequence, modulate sensitivity to biotic and/or abiotic stress, modulate sensitivity to a herbicidal compound, alter post-translational modifications (e.g., phosphorylation sites), transport a translated product to a compartment inside or outside of the cell, improve protein stability, insert or delete cell signaling motifs, etc.

In some preferred embodiments, the transcribable polynucleotide molecule may comprise a nucleic acid sequence that is involved in abiotic stress resistance, activity of a polyketide synthase complex, bacterial disease resistance, biofuel production, biopolymer production, carbohydrate content, cell wall components, enhanced animal and human nutrition, enzyme production, flavor production, growth and development, herbicide tolerance, high protein production, isoprenoid content, modified amino acid content, modified biomass yield, modified fatty acid/oil content, modified oils production, nitrogen utilization, photosynthesis capacity, production of pharmaceutical molecules, production of pigments, virus resistance.

Due to the degeneracy of the genetic code, different nucleotide codons may be used to code for a particular amino acid. A host cell or a cellular organelle often displays a preferred pattern of codon usage. Transcribable polynucleotide molecules are preferably constructed to utilize the codon usage pattern of the particular host cell or host organelle. This generally enhances the expression of the transcribable polynucleotide sequence in a transformed host cell. Any of the above described nucleic acid and amino acid sequences may be modified to reflect the preferred codon usage of a host cell or organism in which they are contained. Such altered sequences may be generated by the Reverse Translate software, which is a codon-optimization software that can be found on the World Wide Web at bioinformatics.org/sms2/rev_trans.html. In some other instances, codon optimization may be done manually by altering the third degenerate bases of codons according to the degeneracy of the genetic code. For example, modification of a transcribable polynucleotide sequence for optimal codon usage in plants is described in U.S. Pat. No. 5,689,052. When so desired, the transcribable polynucleotide molecules of interest can be targeted to the chloroplast, and may be codon-optimized for expression in the chloroplast to account for differences in codon usage between the nucleus and this organelle. In this manner, the polynucleotide of interest may be synthesized using chloroplast-preferred codons. See, e.g., U.S. Pat. No. 5,380,831; PCT Appl. No. WO2011034863. For example, by optimizing codon usage of a GFP reporter gene to reflect the codon bias of the *Chlamydomonas reinhardtii* chloroplast genome, Franklin et al. (*Plant J.* 30:733-744, 2002) were able to increase GFP accumulation by ≈80-fold.

Additional variations in the transcribable polynucleotide molecules may encode proteins having equivalent or superior characteristics when compared to the proteins from which they are engineered. Mutations may include, but are not limited to, deletions, insertions, truncations, substitutions, fusions, shuffling of motif sequences, and the like. Mutations to a transcribable polynucleotide molecule may be introduced in either a specific or random manner, both of which are well known to those of skill in the art of molecular biology.

Thus, one embodiment of the invention is a regulatory element such as provided in SEQ ID NO: 1 through SEQ ID NO: 16; or any complement thereof, or any fragment thereof, or any cis-acting element thereof, operably linked to a transcribable polynucleotide molecule so as to modulate transcription of said transcribable polynucleotide molecule at a desired level or in a desired cellular organelle or developmental pattern upon introduction of said construct into a host cell. In one embodiment, the transcribable polynucleotide molecule comprises a protein-coding region of a gene, and the regulatory element affects the transcription of a functional mRNA molecule that is translated and expressed as a protein product. In another embodiment, the transcribable polynucleotide molecule comprises an antisense region of a gene, and the regulatory element controls the transcription of an antisense RNA molecule, an interfering RNA molecule, or other similar inhibitory RNA in order to inhibit expression of a specific RNA molecule of interest in a target host cell.

Making Recombinant Organisms

In one aspect of the present invention, provided are compositions and methods useful for introducing a polypeptide or polynucleotide into an organism or a cell. "Introducing" is intended to mean presenting to the organism or cell the polypeptide or polynucleotide in such a manner that the sequence gains access to the interior of a cell of the organism. The methods of the invention do not depend on a particular method for introducing a sequence into an organism or cell type, only that the polypeptide or polynucleotide gains access to the interior of at least one cell of the organism. For example, when transforming an algal species, cells with any morphology such as filamentous thallus, a spore, a foliose thallus, a culture cell or a protoplast can be used.

Methods for introducing a polypeptide or polynucleotide into organism are well known in the art including, but not limited to, stable transformation methods, transient transformation methods, virus-mediated methods, and breeding. "Stable transformation" is intended to mean that the nucleic acid construct introduced into an organism integrates into the genome of the organism and is capable of being inherited by the progeny thereof. "Transient transformation" is intended to mean that a polynucleotide is introduced into the organism and does not integrate into the genome or a polypeptide is introduced into an organism.

As such, the isolated nucleic acid molecules of the present invention can be introduced into a host cell either with or without being part of a recombinant transformation vector. In some preferred embodiments, a plasmid vector or a virus-based vector can be used. As described in detail below, common methods and techniques that can be used to prepare recombinant DNA vectors suitable for transformation of host cells, e.g., algae cells and plant cells, as well as methods for transforming a wide variety of algae and higher plant species are well known and described in the technical and scientific literature.

Recombinants Constructs and Vectors

In some embodiments, to use the regulatory elements of the present invention, recombinant nucleic acid constructs including transformation vectors can be prepared. The construct can be made using standard recombinant DNA techniques (see, e.g., Sambrook et al., 1989, supra) and can be introduced into the species of interest by, for example, electroporation, biolistic bombardment, *Agrobacterium*-mediated transformation, or by other means of transformation, for example, as disclosed in greater detail further below.

As used herein, the term "construct" is intended to mean any recombinant polynucleotide molecule such as an expression cassette, plasmid, cosmid, virus, autonomously replicating polynucleotide molecule, phage, or linear or circular, single-stranded or double-stranded, DNA or RNA polynucleotide molecule, derived from any source, capable of genomic integration or autonomous replication, comprising a polynucleotide molecule where one or more polynucleotide molecule has been linked in a functionally operative manner, i.e. operably linked. As used herein, the term "vector" refers to a recombinant polynucleotide construct designed for transfer between host cells, and that may be used for the purpose of transformation, i.e. the introduction of heterologous DNA into a host cell. As such, the term "vector" as used herein sometimes refers to a replicon, such as a plasmid, phage, or cosmid, into which another DNA segment may be inserted so as to bring about the replication of the inserted segment. Generally, a vector is capable of replication when associated with the proper control elements. The term "vector" includes cloning vectors and expression vectors, as well as viral vectors and integrating vectors. An "expression vector" is a vector that includes a regulatory region, thereby capable of expressing DNA sequences and fragments in vitro and/or in vivo.

Methods are known in the art for assembling and introducing constructs into a cell in such a manner that the transcribable polynucleotide molecule is transcribed into a functional mRNA molecule that is translated and expressed as a protein product. For the practice of the present invention, conventional compositions and methods for preparing and using constructs and host cells are well known to one skilled in the art, see for example, Sambrook et al., *Molecular Cloning: A Laboratory Manual*, 3rd edition Volumes 1, 2, and 3 (2000), Cold Spring Harbor Laboratory Press. The vector backbone may be any of those typically used in the field of molecular biology such as plasmids, viruses, artificial chromosomes, BACs, YACs, PACs and vectors such as, for instance, bacteria-yeast shuttle vectors, lamda phage vectors, T-DNA fusion vectors and plasmid vectors (see, for example, Shizuya et al. *Proc. Natl. Acad. Sci. USA,* 1992; Hamilton et al. *Proc. Natl. Acad. Sci. USA,* 1996; Burke et al., *Science,* 1987; Sternberg N. et al., *Proc. Natl. Acad. Sci.*

USA, 1990; Bradshaw et al., *Nucl Acids Res*, 1995; Frischaufetal., *J. Mol. Biol.*, 1983; and Walden et al., *Mot Celt Biol.*, 1990).

Various untranslated regulatory sequences may be included in the nucleic acid vectors disclosed herein. Any such regulatory sequences may be provided in a vector with other regulatory sequences. Such combinations can be designed or modified to produce desirable regulatory features. Constructs of the present invention would typically comprise one or more gene expression regulatory elements operably linked to a transcribable polynucleotide molecule which itself is operably linked to a 3' transcription termination polynucleotide molecule. Recombinant nucleic acid constructs of the present invention may also include additional 5' untranslated regions (5' UTR) of an mRNA polynucleotide molecule or gene which can play an important role in translation initiation. Recombinant vectors may also include, for example, origins of replication, scaffold attachment regions (SARs), markers, transcriptional enhancers, translational enhancers, and introns. These additional regulatory polynucleotide molecules may be derived from a source that is native or heterologous with respect to the other elements present on the construct.

A transformation vector comprising a polynucleotide molecule of the present invention will typically comprise a marker gene that confers a selectable or scorable phenotype on target host cells, e.g., algal cells or plant cells. A number of selectable markers have been successfully developed for efficient isolation of genetic transformants of algae. Such markers are known. Common selectable markers include antibiotic resistance, fluorescent markers, and biochemical markers. Several different antibiotic resistance genes have been used successfully for microalgal transformant selection, including blasticidin (Tamura, *Biosci. Biotechnol. Biochem.* 59:2336-2338, 1995; U.S. Pat. Appl. No. US20090317857A1), bleomycin (see, for example, Apt et al., 1996, supra; Fischer et al., 1999, supra; Fuhrmann et al., *Plant J.*, 1999, Lumbreras et al., *Plant J.* 1994; Zaslayskaia et al., *J. Phycol.* 2000), chloramphenicol (Poulsen and Kroger, *FEBS Lett.*, 2005), hygromycin (Berthold et al., 2002, supra), G418 (Dunahay et al., 1995, supra; Poulsen and Kroger, *FEBS Lett.*, 2005, Zaslayskaia et al., 2000, supra), nourseothricin (Zaslayskaia et al., *J. Phycol.* 2000), paromomycin (Jakobiak et al., *Protist*, 2004; Sizova et al., *Gene*, 2001), spectinomycin (Cerutti et al., *Genetics*, 1997; Doetsch et al., *Curr. Genet.* 2001; Fargo, *Mol. Cell. Biol.* 19:6980-90, 1999), streptomycin (Berthold et al., *Protist*, 2002), and many others. Additional selectable markers for use in microalgae such as *Chlamydomonas* can be markers that provide resistance to kanamycin and amikacin resistance (Bateman, *Mol. Gen. Genet.* 263:404-10, 2000), zeomycin and phleomycin resistance (Stevens, *Mol. Gen. Genet.* 251:23-30, 1996), and paromomycin and neomycin resistance (Sizova, *Gene* 277:221-9, 2001). Other fluorescent or chromogenic markers that have been used include luciferase (Falciatore et al., *J. Mar. Biotechnol.*, 1999; Fuhrmann et al., *Plant Mol. Biol.*, 2004; Jarvis and Brown, *Curr. Genet.*, 1991), β-glucuronidase (Chen et al., *Curr. Genet.* 2001; Cheney et al., *J. Phycol.*, 2001; Chow and Tung, *Plant Cell. Rep.*, 1999; El-Sheekh, *Biol. Plant* 1999; Falciatore et al., *J. Mar. Biotechnol.*, 1999; Kubler et al., *J. Mar. Biotechnol.* 1994), β-galactosidase (Gan et al., *J. Appl. Phycol.*, 2003; Jiang et al., *Plant Cell Rep.*, 2003; Qin et al., *High Technol. Lett.*, 2003), and green fluorescent protein (GFP) (Cheney et al., 2001, supra; Ender et al., *Plant Cell*, 2002, Franklin et al., *Plant J.*, 2002; 56, 148, 210).

One or more additional promoters may also be included in the recombinant constructs. These promoters may be operably linked to any of the transcribable polynucleotide sequences described above. Alternatively, the promoters may be operably linked to other nucleic acid sequences, such as those encoding transit peptides, selectable marker proteins, or antisense sequences. These additional promoters may be selected on the basis of the cell type or organelle into which the vector will be inserted. Promoters which function in various host organisms such as algae, animals, bacteria, fungi, and plants are all well taught in the art. The additional promoters may also be selected on the basis of their regulatory features. Examples of such features include enhancement of transcriptional activity, inducibility, tissue-specificity, and developmental stage-specificity.

Translational enhancers may also be incorporated as part of a recombinant nucleic acid vector in accordance with the present invention. Thus the recombinant vector may preferably contain one or more 5' cis-acting sequences and leader sequences which serve to enhance expression of the nucleic acid sequence. Such enhancer sequences, as described in detail above, may be desirable to increase or alter the translational efficiency of the resultant mRNA.

One skilled in the art would readily appreciate that a variety of promoter sequences can be usefully deployed for transformation systems of microalgal species in accordance with the present invention. For example, the promoters commonly used to drive transgene expression in microalgae include various versions of the of cauliflower mosaic virus promoter 35S (CaMV35S), which is the typical heterologous promoter used in dinoflagellates and chlorophyta (Chow et al, *Plant Cell Rep.*, 18:778-780, 1999; Jarvis and Brown, *Curr. Genet.*, 317-321, 1991; Lohuis and Miller, *Plant J.*, 13:427-435). The SV40 promoter from simian virus has also reported to be active in several algae (Gan et al., *J. Appl. Phycol.*, 151 345-349, 2003; Qin et al., *Hydrobiologia* 398-399, 469-472, 1999). The promoters of RBCS2 (ribulose bisphosphate carboxylase, small subunit) (Fuhrmann et al., *Plant J.*, 19:353-361) and PsaD (abundant protein of photosystem I complex) (Fischer and Rochaix, *FEBS Lett.* 581:5555-5560, 2001) from *Chlamydomonas* can also be useful. The fusion promoters of HSP70A/RBCS2 and HSP70A/β2TUB (tubulin) (Schroda et al., *Plant J.*, 21:121-131, 2000) can also be useful for an improved expression of transgenes, in which HSP70A promoter may serve as a transcriptional activator when placed upstream of other promoters. High-level expression of a gene of interest can also be achieved in, for example diatoms species, under the control of a promoter of the fcp gene encoding the fucoxanthin-chlorophyll binding protein (Falciatore et al., *Mar. Biotechnol.*, 1:239-251, 1999; Zaslayskaia et al., *J. Phycol.* 36:379-386, 2000). If so desired, inducible promoters can provide rapid and tightly controlled expression of genes in transgenic microalgae. For example, promoter regions of the NR genes encoding nitrate reductase can be used as such inducible promoters. The NR promoter activity is suppressed by ammonium and induced when ammonium is replaced by nitrate (Poulsen and Kroger, *FEBS Lett* 272: 3413-3423, 2005), thus gene expression can be switched off or on when microalgal cells are grown in the presence of ammonium/nitrate.

In some embodiments, polynucleotide of interest may be targeted to the chloroplast. In this manner, while the polynucleotide of interest is not inserted into the chloroplast, the expression cassette will additionally contain a nucleic acid encoding a transit peptide to direct the gene product of interest to the chloroplast. Such transit peptides, also known as chloroplast-targeting sequences, are known in the art and include the chloroplast small subunit of ribulose-1,5-bisphosphate carboxylase (Rubisco) (de Castro Silva Filho et al., *Plant Mot Biol.* 30: 769-780, 1996; Schnell et al., *J. Biol. Chem.* 266: 3335-3342, 1991; van den Broeck et al., Nature 313:35 S-363, 1985); 5-(enolpyruvyl)shikimate-3-phosphate synthase (EPSPS) (Archer et al., *J. Bioenerg. Biomemb.* 22: 789-810, 1990); tryptophan synthase (Zhao et al., *J. Biol. Chem.* 270: 6081-6087, 1995); plastocyanin (Lawrence et al., *J. Biol. Chem.*, 272: 20357-20363, 1997); chorismate synthase (Schmidt et al., *J. Biol. Chem.* 268(36): 27447-27457, 1993); and the light harvesting chlorophyll alb binding protein (LHBP) (Lamppa et al., *J. Biol. Chem.* 263: 14996-14999, 1988; Kavanagh et al., *Mol Gen Genet.* 215:38-45, 1988). See also Von Heijne et al., *Plant Mol. Biol. Rep.* 9: 104-126, 1991; Clark et al., *J. Biol. Chem.* 264: 17544-17550, 1989; Della-Cioppa et al., *Plant Physiol.* 84: 965-968, 1987; Romer et al., *Biochem. Biophys. Res. Commun.* 196: 1414-1421, 1993; and Shah et al., *Science* 233: 478-481, 1986. In microalgae, a number of chloroplast targeting sequences have been identified and may be suitable for the methods of the present invention. Sequence requirements specific for chloroplast vectors for genetic engineering of the green alga, *Chlamydomonas reinhardtii*, have been known since 1980s. More recent examples of such sequences include a chloroplast-targeting signal identified in the sulfate permease gene SuIP of *Chlamydomonas reinhardtii* (Chen et al., *Planta,* 218:98-106, 2003). When expression in the chloroplast is desired, the transcribable polynucleotides of interest to be targeted to the chloroplast may be optimized for expression in the chloroplast to account for differences in codon usage between the nucleus and this organelle. In this manner, the polynucleotide of interest may be synthesized using chloroplast-preferred codons. See, for example, U.S. Pat. No. 5,380,831; PCT Appl. No. WO2011034863.

Transformation Techniques

A number of methods and techniques useful for genetic transformation of microorganisms are well known in the art, and can be deployed for the methods of the present invention. Such genetic transformation can result in stable insertion and/or expression of transgenes from either the nucleus or the plastid, and in some cases can result in transient expression of transgenes. For example, genetic transformation of microalgae has been reported successful for more than 30 different strains of microalgae, which belong to at least ~22 species of green, red, and brown algae, diatoms, euglenids, and dianoflagellates (see, e.g., Radakovits et al., *Eukaryotic Cell,* 2010; Gong et al., *J. Ind. Microbiol. Biotechnol.*, 2011). Therefore, it will be appreciated by one skilled in the art that a variety of transformation methods can be used to introduce DNA molecules into microalgal cells, including agitation in the presence of glass beads or silicon carbide whiskers as reported by, for example, Dunahay, *Biotechniques,* 1993; Kindle, *Proc. Natl. Acad. Sci. U.S.A.,* 1990; Michael and Miller, *Plant J.,* 1998. Electroporation techniques have been successfully used for genetic transformation of several microalgal species including *Nannochloropsis* sp. (see, e.g., Chen et al., *J. Phycol.* 2008), *Chlorella* sp. (see, e.g., Chen et al., *Curr. Genet.* 2001; Chow et al., *Plant Cell Rep.* 1999), *Chlamydomonas* (Shimogawara et al., *Genetics,* 1998), *Dunaliella* (Sun et al., *Mol. Biotechnol.* 2005). Micro-projectile bombardment, also referred to as micro-particle bombardment, gene gun transformation, or biolistic bombardment, has been used successfully for several algal species including, for example, *Phaeodactylum* (Apt et al., *Mol. Gen. Genet.,* 1996), diatoms species *Cyclotella* and *Navicula* (Dunahay et al., *J. Phycol.,* 1995), diatom *Cylindrotheca* (Fischer et al., *Phycol.,* 1999), *Chlorella* (El-Sheekh, *Biol. Plant.,* 1999), *Volvox* species (Jakobiak et al., *Protist,* 2004). Additionally, *Agrobacterium*-mediated gene transfer techniques can also be useful for genetic transformation of microalgae, as has been reported by, for example, Kumar et al., *Plant Sci.,* 2004, and Cheney et al., *J. Phycol.,* 2001).

It will also be apparent to the skilled artisan that a number of well-known methods and techniques for transformation of chloroplasts of plant species and algal species may be used for the methods disclosed herein. See, for example, Svab et al., *Proc. Natl. Acad. Sci. USA* 87: 8526-8530, 1990; Svab and Maliga *Proc. Natl. Acad. Sci. USA* 90: 913-917, 1993; Svab and Maliga, *EMBO J.* 12: 601-606, 1993. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (*Proc. Natl. Acad. Sci. USA* 91: 7301-7305, 1994). As will be appreciated by a skilled artisan, a variety of methods and techniques that have been used successfully for chloroplast transformation of several species of the marine red microalga *Porphyridium* (Lapidot et al., *Plant Physiol,* 129:7-12, 2002), and algal species of *Dunaliella* and *Scenedesmus* (see, for example, PCT Appl. No. WO2011034863) can be deployed for the methods disclosed herein. Typically, an expression cassette comprising a nucleic acid molecule of the present invention, once stably transformed into a chloroplast of a host cell where the DNA is stably integrated, will be inherited through organelle replication in daughter cells.

As described above, the transcribable polynucleotides of interest to be targeted to the chloroplast may be codon-optimized for expression in the chloroplast to account for differences in codon usage between the nucleus and this organelle. In this manner, the polynucleotide of interest may be synthesized using chloroplast-preferred codons. See, for example, U.S. Pat. No. 5,380,831; PCT Appl. No. WO2011034863.

Host Cell

Suitable host cells to modify using the materials and methods according to the present invention include, but are not limited to, bacteria, protist, microalga, phytoplankton, fungus, protozoa, and plant. Host cells can be either untransformed cells or cells that are already transfected with at least one nucleic acid molecule.

In principle, the methods and compositions according to the present invention can be deployed for any microbial species, including, but not limited to, microalgae and microfungi. The methods and compositions are preferably used with microorganisms that are important or interesting for aquaculture, agriculture, for the production of biomass used in producing liquid fuel molecules and other chemicals. Suitable species may include members of the genera *Amphora, Anabaena, Ankistrodesmus, Aplanochytrium, Arthrospira, Botryococcus, Chaetoceros, Chlamydomonas, Chlorella, Chlorococcum, Chrococcidiopsis, Chrysophyceae, Colwellia, Cricosphaera, Crypthecodinium, Crypthecodinium cohnii, Cryptococcus curvatus, Cunninghamella, Cyclotella, Dunaliella, Elina, Elina marisalba, Elina sinorifica, Gleocapsa, Isochrysis, Isochrysis galbana, Japanochytrium, Labrinthula, Labyrinthomyxa, Labyrinthula, Leptolyngbya, Lyngbya, Microcoleus, Monodus,*

Monoraphidium, Moritella, Mortierella, Mucor, Mucor circinelloides, Mucor mecdo, Nannochloris, Nannochloropsis, Navicula, Neochloris, Nitzschia, Ochromonas, Oocystis, Oscillatoria, Ostreococcus, Parietochloris, Pavlova, Phaeodactylum, Photobacterium, Pichia, Pithium, Pleurochrysis, Pleurococcus, Porphyridium, Pseudoalteromonas, Pseudoanabaena, Psychromonas, Pyramimonas, Rhodosporidium, Scenedesmus, Schizochytrium, Shewanella, Skeletonema, Spirulina, Stichococcus, Synechococcus, Synechocystis, Tetraselmis, Thalassiosira, Thermosynechococcus, Thraustochytrium, Ulkenia, and Vibrio.

Non-limiting examples of preferred species include, for instance, Mortierella schmuckeri, Shewanella olleyana, Aplanochytrium kerguelensis, Crypthecodinium cohnii, Cryptococcus curvatus, Cunninghamella, Cunninghamella echinulata, Cunninghamella elegans, Dunaliella salina, Dunaliella viridis, Dunaliella tertiolecta, Haematococcus pluvialis, Elina marisalba, Elina sinorifica, Isochrysis galbana, Japanochytrium, Japanochytrium marinum, Labyrinthomyxa pohlia, Labyrinthomyxa sauvageaui, Labyrinthula algeriensis, Labyrinthula chattonii, Labyrinthula cienkowskii, Labyrinthula coenocystis, Labyrinthula macrocystis, Labyrinthula macrocystis atlantica, Labyrinthula macrocystis macrocystis, Labyrinthula magnifica, Labyrinthula minuta, Labyrinthula pacifica, Labyrinthula roscoffensis, Labyrinthula valkanovii, Labyrinthula vitellina, Labyrinthula zopfii, Labyrinthuloides minuta, Labyrinthuloides schizochytrops, Monodus subterraneus, Monoraphidium, Moritella marina, Mortierella alpina, Mortierella isabellina, Mortierella ramannia, Mucor circinelloides, Mucor mecdo, Nannochloropsis gaditana, Nannochloropsis granulate, Nannochloropsis limnetica, Nannochloropsis oceanic, Nannochloropsis oculata, Nannochloropsis salina, Nitzschia alba, Nitzschia laeva, Nitzschia laevis, Pavlova lutheri, Parietochloris incise, Phaeodactylurn cruentum, Phaeodactylum tricomutum, Photobacterium profundum, Pithium insidiosum, Pichia pastoris, Rhodosporidium toruloides, Schizochytrium aggregatum, Schizochytrium limacinum, Schizochytrium mangrovei, Schizochytrium minutum, Schizochytrium octosporum, Scenesdemus dimorphus, Scenesdemus obliquus, Shewanella japonica, Tetraselmis suecica, Thraustochytrium aggregatum, Thraustochytrium arudimentale, Thraustochytrium aureum, Thraustochytrium benthicola, Thraustochytrium globosum, Thraustochytrium kinnei, Thraustochytrium motivum, Thraustochytrium pachydermum, Thraustochytrium proliferum, Thraustochytrium roseum, Thraustochytrium striatum, Ulkenia amoeboida, Ulkenia minuta, Ulkenia profunda, Ulkenia radiata, Ulkenia radiate, Ulkenia sarkariana, Ulkenia sp. BP-5601, Ulkenia visurgensis, and Vibrio marinus, In some embodiments of the present application, preferred microorganisms to genetically modify include, but are not limited to, photosynthetic organisms such as cyanobacteria, algae, diatoms, and the like. Exemplary diatoms may include members of the genera Achnanthes, Amphora, Chaetoceros, Coscinodiscus, Cylindrotheca, Cyclotella, Cymbella, Hantzschia, Navicula, Nitzschia, Pavlova, Pseudo-Nitzschia, Phaeodactylum, Psammodictyon, Skeletonema, Thalassionema, and Thallasiosira. Preferred host cells for use in the present invention include microorganisms from a genus including, but not limited to: Dunaliella, Labyrinthuloides, Japonochytrium, Scenedesmus, Schizochytrium, and Thraustochytrium. Particularly preferred organisms in some embodiments include, but are not limited to, any microorganism of the genus Nannochloropsis. Preferred species within the genus Nannochloropsis include, but are not limited to, N. gaditana, N. granulata, N. limnetica, N. oceanica, N. oculata, and N. salina. Particularly preferred strains of this genus include, but are not limited to: Nannochloropsis gaditana CCMP1894, Nannochloropsis oculata CCMP525, and Nannochloropsis salina CCMP537.

The discussion of the general methods given herein is intended for illustrative purposes only. Other alternative methods and embodiments will be apparent to those of skill in the art upon review of this disclosure, and are to be included within the spirit and purview of this application.

It should also be understood that the following examples are offered to illustrate, but not limit, the invention.

EXAMPLES

Example 1

Identification and Isolation of Regulatory Elements from Nannochloropsis

Applicants of the present application identified and isolated polynucleotides having gene regulatory activity from the genome sequence data of the single-cell microalga Nannochloropsis gaditana. Briefly, whole-cell genomic DNA content of the microalgal strain N. gaditana CCMP1894, including nuclear and plastid genomes, was isolated and subsequently sequenced by using a whole-genome shotgun sequencing approach as described in PCT Patent Publication No. WO2010115156A2. Additionally, cDNA pools derived from Nannochloropsis cell culture were generated and sequenced by using the procedures described in US Pat. Publication No. US20110182862A1. After sequence assembly step, coding gene sequences were predicted from assembled contigs using an approach that combined evidence from multiple sources using the Evigan consensus gene prediction method as described previously by Liu et al. [Bioinformatics, March 1; 24(5):597-605.2008]. Mapping of cDNA sequences onto assembled genomic sequence allowed the identification of introns, 5'-UTRs, and 3'-UTRs.

In silico analyses of the annotated genome sequence of N. gaditana CCMP1894 revealed several genes encoding putative ribosomal proteins as well as a gene encoding a Nannochloropsis homolog of the translationally controlled tumor protein (TCTP) (Bommer et al., J. Biochem. Cell Biol. 36:379-385, 1993; Masura et al., Plant Physiol. Biochem. 49:701-708, 2011). Applicants designed oligonucleotides primers against each of the genes and recovered the genomic DNA regions upstream of the coding sequences, i.e. promoter regions (TABLE 2). Transformation vectors were constructed and subsequently used to generate transgenic cells in order to test and evaluate the promoter activity of each of the promoter regions.

Algal Strain and Culture Conditions:

Nannochloropsis gaditana algal strain was obtained from the Provasoli-Guillard National Center for Marine Algae and Microbiota (NCMA, Maine, U.S.A.), which is formerly the National Center for Culture of Marine Phytoplankton (CCMP). Cultures were grown in 50 mL of medium in 250 mL shake flasks at 100 rpm on a 0.75 inch orbital shaker under 50 1JE constant light, 1% $CO_2$, 25° C. Light intensity was measured using LI-COR Light Meter, LI-250A.

PM024 medium was prepared by dissolving 35 g of Instant Ocean salts, 200 mL of f/2 SOX concentrate (Sigma G0154) and MilliQ filtered water to make 1 L. The solution was filt~r sterilized by passage through a 0.2 micron bottle top filter (Corning #430513). Zeocin was supplied when at 51 Jg/ml. Cell density was measured by flow cytometry using an Accuri cytometer.

Genomic DNA Isolation:

Mid-log phase *Nannochloropsis* cells from a 10-mL culture were collected by centrifugation at 2500×g for 10 min at 4° C., supernatant was removed and the cell pellet was used for high-molecular weight DNA extraction using the Meta-G-Nome™ DNA Isolation Kit from Epicenter Biotechnologies according to the manufacturer's recommended protocol, with minor modifications. Purified gDNA was quantitated with a NanoDrop® Spectrophotometer and stored −20° C.

TABLE 2

PCR primers used for PCR amplification of each of the *Nannochloropsis* regulatory regions.

| Regulatory Region | Length | PCR Primer 1 | PCR Primer 2 |
|---|---|---|---|
| TCTP promoter (SEQ ID NO: 1) | 1000 | oSGI-JU-106 (SEQ ID NO: 29) | oSGI-JU-107 (SEQ ID NO: 30) |
| Ribosomal protein-L13e (SEQ ID NO: 2) | 1000 | oSGI-JU-91 (SEQ ID NO: 17) | oSGI-JU-92 (SEQ ID NO: 18) |
| Ribosomal protein-L4 (SEQ ID NO: 3) | 1000 | oSGI-JU-93 (SEQ ID NO: 19) | oSGI-JU-94 (SEQ ID NO: 20) |
| Ribosomal protein-RP-L5 (SEQ ID NO: 4) | 961 | oSGI-JU-95 (SEQ ID NO: 21) | oSGI-JU-96 (SEQ ID NO: 22) |
| RP-S4e promoter (SEQ ID NO: 5) | 444 | oSGI-JU-97 (SEQ ID NO: 23) | oSGI-JU-98 (SEQ ID NO: 24) |
| RP-S8e promoter (SEQ ID NO: 6) | 961 | oSGI-JU-99 (SEQ ID NO: 25) | oSGI-JU-100 (SEQ ID NO: 26) |

Example 2

Construction of Recombinant Expression Cassettes Containing Regulatory Regions from *Nannochloropsis*

This Example describes the design and construction of expression cassettes and transformation vectors that were subsequently used to evaluate the promoter activity of several regulatory regions disclosed herein.

Briefly, each of the regulatory regions was operably cloned upstream of a reporter gene TurboGFP gene (Evrogen, Moscow, Russia) such that its ability to drive expression of the TurboGFP gene, i.e. promoter activity, could be subsequently tested and evaluated via green fluorescence analysis of recombinant *Nannochloropsis* cells upon genetic transformation. As positive control, a promoter region of the eukaryotic initiation elongation eIF3 of *N. gaditana*, which had been characterized previously, was used to drive TurboGFP expression in a transformation vector named pSGE05140.

pSGI-JU-38 is a plasmid for transformation of *Nannochloropsis* cells to express TurboGFP reporter gene under control of the *N. gaditana* TCTP promoter (SEQ ID NO: 1). This plasmid was constructed by inserting the *N. gaditana* TCTP promoter sequence and the 5' 150 bp of the TurboGFP coding sequence into a NarI-digested pSGE05140 vector by using the In-Fusion® cloning system (Clontech). In the sequence of pSGE05140 vector, restriction enzyme NarI cuts at 150 bp into the TurboGFP coding sequence and at the 5' end of the *N. gaditana* eIF3 promoter. To generate the cloning insert, two PCR half products were first generated in separate amplification reactions. The 5'-half PCR product, corresponding to the *N. gaditana* TCTP promoter, was amplified from *N. gaditana* genomic DNA by using primers oSGI-JU-106 (SEQ ID NO: 29) and pSGI-JU-107 (SEQ ID NO: 30). Primer oSGI-JU-106 had a 15-bp 5' extension that overlapped with the 15 bp nucleotides adjacent to the NarI cut site at the 5' end of the *N. gaditana* eIF3 promoter in pSGE05140 vector and primer oSGI-JU-107 had a 15 bp 5' extension that overlapped with the first 15 bp of the TurboGFP coding sequence. The 3'-half PCR product, corresponding to the 5' 150 bp of the TurboGFP, was amplified from pSGE05140 template by using primers oSGI-JU-104 (SEQ ID NO: 27) and oSGI-JU-105 (SEQ ID NO: 28). These primers were designed to generate a PCR product that starts with the ATG of TurboGFP and ends 15 bp 3' of the NarI cut site within the TurboGFP gene in the pSGE05140 vector. The plasmid product resulting from a 3-way In-Fusion® assembly reaction, named pSGI-JU-38, was confirmed by sequencing. A diagrammatic representation of plasmid pSGI-JU-38 is shown at FIG. 1.

pSGI-JU-33 is a recombinant vector for nuclear transformation to express TurboGFP reporter gene under control of the *N. gaditana* RP-L13e promoter (SEQ ID NO 2). This plasmid was constructed using a strategy similar to that used for the construction of pSGI-JU-38 as described above. Briefly, the cloning vector was pSGE05140 also pre-digested with restriction enzyme NarI. To generate the cloning insert, two PCR half products were first generated in separate amplification reactions. The 5'-half PCR product, corresponding to the *N. gaditana* RP-L13e promoter, was amplified from *N. gaditana* genomic DNA by using primers oSGI-JU-91 (SEQ ID NO: 17) and oSGI-JU-92 (SEQ ID NO: 18). Primer oSGI-JU-91 had a 15-bp 5' extension that overlapped with the 15 bp nucleotides adjacent to the NarI cut site at the 5' end of the *N. gaditana* eIF3 promoter in pSGE05140 vector and primer oSGI-JU-92 had a 15 bp 5' extension that overlapped with the first 15 bp of the TurboGFP coding sequence. The 3'-half PCR product, corresponding to the 5' 150 bp of the TurboGFP, was amplified from pSGE05140 template by using primers oSGI-JU-104 (SEQ ID NO: 27) and oSGI-JU-105 (SEQ ID NO: 28). These primers were designed to generate a PCR product that starts with the ATG of TurboGFP and ends 15 bp 3' of the NarI cut site within the TurboGFP gene in the pSGE05140 vector. The plasmid product resulting from a 3-way In-Fusion® assembly reaction, which was named pSGI-JU-33, was subsequently confirmed by sequencing.

pSGI-JU-34 is a recombinant vector for nuclear transformation to express TurboGFP reporter gene under control of the *N. gaditana* RP-L4 promoter (SEQ ID NO: 3). This plasmid was constructed using a strategy similar to that used for the construction of pSGI-JU-38 as described above. Briefly, the cloning vector was pSGE05140 also pre-digested with restriction enzyme NarI. To generate the cloning insert, two PCR half products were first generated in separate amplification reactions. The 5'-half PCR product, corresponding to the *N. gaditana* RP-L4 promoter, was amplified from *N. gaditana* genomic DNA by using primers oSGI-JU-93 (SEQ ID NO: 19) and oSGI-JU-94 (SEQ ID NO: 20). Primer oSGI-JU-93 had a 15-bp 5' extension that overlapped with the 15 bp nucleotides adjacent to the NarI cut site at the 5' end of the *N. gaditana* eIF3 promoter in pSGE05140 vector and primer oSGI-JU-94 had a 15 bp 5' extension that overlapped with the first 15 bp of the TurboGFP coding sequence. The 3'-half PCR product, corresponding to the 5' 150 bp of the TurboGFP, was amplified from pSGE05140 template by using primers oSGI-JU-104 (SEQ ID NO: 27) and oSGI-JU-105 (SEQ ID NO: 28). These primers were designed to generate a PCR product that starts with the ATG of TurboGFP and ends 15 bp 3' of the NarI cut site within the TurboGFP gene in the pSGE05140 vector. The plasmid product resulting from a 3-way In-Fusion® assembly reaction, which was named pSGI-JU-34, was subsequently confirmed by sequencing.

pSGI-JU-35 is a recombinant vector for nuclear transformation to express TurboGFP reporter gene under control of the *N. gaditana* RP-L5 promoter (SEQ ID NO: 4). This plasmid was constructed using a strategy similar to that used for the construction of pSGI-JU-38 as described above. Briefly, the cloning vector was pSGE05140 also pre-digested with restriction enzyme NarI. To generate the cloning insert, two PCR half products were first generated in separate amplification reactions. The 5'-half PCR product, corresponding to the *N. gaditana* RP-L4 promoter, was amplified from *N. gaditana* genomic DNA by using primers oSGI-JU-95 (SEQ ID NO: 21) and oSGI-JU-96 (SEQ ID NO: 22). Primer oSGI-JU-95 had a 15-bp 5' extension that overlapped with the 15 bp nucleotides adjacent to the NarI cut site at the 5' end of the *N. gaditana* eIF3 promoter in pSGE05140 vector and primer oSGI-JU-96 had a 15 bp 5' extension that overlapped with the first 15 bp of the TurboGFP coding sequence. The 3'-half PCR product, corresponding to the 5' 150 bp of the TurboGFP, was amplified from pSGE05140 template by using primers oSGI-JU-104 (SEQ ID NO: 27) and oSGI-JU-105 (SEQ ID NO: 28). These primers were designed to generate a PCR product that starts with the ATG of TurboGFP and ends 15 bp 3' of the NarI cut site within the TurboGFP gene in the pSGE05140 vector. The plasmid product resulting from a 3-way In-Fusion® assembly reaction, which was named pSGI-JU-35, was subsequently confirmed by sequencing.

pSGI-JU-36 is a recombinant vector for nuclear transformation to express TurboGFP reporter gene under control of the *N. gaditana* RP-S4e promoter (SEQ ID NO: 5). This plasmid was constructed using a strategy similar to that used for the construction of pSGI-JU-38 as described above. Briefly, the cloning vector was pSGE05140 also pre-digested with restriction enzyme NarI. To generate the cloning insert, two PCR half products were first generated in separate amplification reactions. The 5'-half PCR product, corresponding to the *N. gaditana* RP-S4e promoter, was amplified from *N. gaditana* genomic DNA by using primers oSGJ-JU-97 (SEQ ID NO: 23) and oSGI-JU-98 (SEQ ID NO: 24). Primer oSGJ-JU-97 had a 15-bp 5' extension that overlapped with the 15 bp nucleotides adjacent to the NarI cut site at the 5' end of the *N. gaditana* eIF3 promoter in pSGE05140 vector and primer oSGI-JU-98 had a 15 bp 5' extension that overlapped with the first 15 bp of the TurboGFP coding sequence. The 3'-half PCR product, corresponding to the 5' 150 bp of the TurboGFP, was amplified from pSGE05140 template by using primers oSGI-JU-104 (SEQ ID NO: 27) and oSGI-JU-105 (SEQ ID NO: 28). These primers were designed to generate a PCR product that starts with the ATG of TurboGFP and ends 15 bp 3' of the NarI cut site within the TurboGFP gene in the pSGE05140 vector. The plasmid product resulting from a 3-way In-Fusion® assembly reaction, which was named pSGI-JU-36, was subsequently confirmed by sequencing.

pSGI-JU-37 is a recombinant vector for nuclear transformation to express TurboGFP reporter gene under control of the *N. gaditana* RP-S8e promoter (SEQ ID NO: 6). This plasmid was constructed using a strategy similar to that used for the construction of pSGI-JU-38 as described above. Briefly, the cloning vector was pSGE05140 also pre-digested with restriction enzyme NarI. To generate the cloning insert, two PCR half products were first generated in separate amplification reactions. The 5'-half PCR product, corresponding to the *N. gaditana* RP-S8e promoter, was amplified from *N. gaditana* genomic DNA by using primers oSGI-JU-99 (SEQ ID NO: 25) and oSGI-JU-100 (SEQ ID NO: 26). Primer oSGI-JU-99 had a 15-bp 5' extension that overlapped with the 15 bp nucleotides adjacent to the NarI cut site at the 5' end of the *N. gaditana* eIF3 promoter in pSGE05140 vector and primer oSGI-JU-100 had a 15 bp 5' extension that overlapped with the first 15 bp of the TurboGFP coding sequence. The 3'-half PCR product, corresponding to the 5' 150 bp of the TurboGFP, was amplified from pSGE05140 template by using primers oSGI-JU-104 (SEQ ID NO: 27) and oSGI-JU-105 (SEQ ID NO: 28). These primers were designed to generate a PCR product that starts with the ATG of TurboGFP and ends 15 bp 3' of the NarI cut site within the TurboGFP gene in the pSGE05140 vector. The plasmid product resulting from a 3-way In-Fusion® assembly reaction, which was named pSGI-JU-37, was subsequently confirmed by sequencing.

Example 3

Genetic Transformation of *Nannochloropsis*

Nuclear Transformation:

Nuclear transformations were carried out with algal cells of the *Nannochloropsis gaditana* strain CCMP1894. Cells were grown at 25° C. in L1–Si+10×N&P medium [i.e., L1 media (Guillard and Hargraves, *Phycologia* 32:234-236, 1993) without silica and with 10× concentration of nitrate and phosphate], 1% $CO_2$, 100 µE light on a 16:8 light dark cycle with agitation using an orbital shaker that was set at 110 rpm. Log-phase cells ($1\text{-}5\times10^7$ cells/mL) were harvested by centrifugation at 2,500×g at 25° C. for 10 min. The supernatant was decanted and cells were washed three times with 50 mL of 385 mM Sorbitol then resuspended at $1\times10^{10}$ cells/mL in 385 mM Sorbitol. One hundred microliter of this cell suspension was mixed with linearized DNA (in a maximum volume of 10 µL) and transferred to a pre-chilled electroporation cuvette (0.2 cm gap). Electroporation of algal cells was performed with an electroporator that was set at 50 µF capacitance, 500Ω resistance and voltage of 2.2 kV. After electroporation, 1 mL of 385 mM Sorbitol was added to the cuvette then the resulting cell suspension was transferred to a 15 mL tube containing 10 mL L1-Si+10×N&P medium. Cells were recovered at room temperature under low light (~5 µE) for 1-2 days. After recovery, cells were collected by centrifugation at 2,500×g at 25° C. for 10 min then resuspended in 500 µL L1-Si+10×N&P medium. Approximately 250 µL of cell suspension are plated onto each L1-Si+10×N&P plates containing Zeocin™ (Invitrogen, Carlsbad, Calif.) at appropriate selective concentration (typically 5 mg/L).

Plastid Transformation:

For chloroplast transformation of algal cells, a particle bombardment procedure is deployed as described in Cohen et al, (*Method. Enzymol.* 297; 192-208, 1998) with minor modifications. Plastid-targeting vectors are designed and constructed to enable the introduction of heterologous sequences to be expressed in the plastid. In a typical chloroplast transformation experiment, the transformation vector contains a selectable marker that includes the coding sequence of an acetohydroxyacid synthase (AHAS) carrying a mutation that confers resistance to an AHAS inhibitor, such as metsulfuron methyl (MSM). *Nannochloropsis* cells are cultured at 30° C. in L1-Si+10×N&P medium, 1% $CO_2$, 100 µE light on a 16:8 light dark cycle with agitation using an orbital shaker that was set at 110 rpm. In most experiments, selection plates are L1-Si+10×N&P agar plates containing an herbicide resistance selection. When the herbicide MSM (Sigma-Aldrich) is used the typical herbicide concentration is 30 µM. Each plate typically has approximately $1 \times 10^{8-9}$ algal cells. DNA coated particles are delivered to the cells using a Biolistic® PDS-1000/He particle delivery system (Bio-Rad, Hercules, Calif.). In some other experiments, algal cells are transformed after plating on L1-Si+10×N&P plates without selection then transferred to plates with selection after recovery of 2-3 days under low light conditions.

Example 4

Molecular Characterization of Transgenic *Nannochloropsis* Cells

In most *Nannochloropsis* transformation experiments where a fluorescence reporter gene was included in the transformation vector, fluorescence microscopy techniques were deployed for the rapid identification of transformed cells and subsequent characterization of the transgenic cells.

In addition, a colony PCR technique was deployed to identify and/or confirm cell lines that were successfully transformed. For colony PCR analysis, *Nannochloropsis* cells from a single colony or 0.5 µL of culture were typically used per 12.5 µL of PCR reaction. Colony PCR was performed to assess the presence of the SV40 promoter and the ble selectable marker using an upstream primer, oSGI-JU-144 (3'-cctctgagctattccagaag-5'; SEQ ID NO: 31), that anneals within the SV40 promoter and a downstream primer, oSGI-JU-145 (3'-aagttcgtggacacgacctc-5'; SEQ ID NO: 32), that anneals to the ble coding sequence.

Colony PCR analyses confirmed that algal colonies obtained from the transformation of each of the vector constructs described in Example 2 contained the SV40-ble expression cassette. As expected, the primers used for colony PCR analyses yielded a PCR product having an expected size of 554-bp.

Southern Blot Analysis

Southern blot techniques were also deployed for the characterization of transformed *Nannochloropsis* cells, by using common protocols and procedures described in, e.g. Sambrook et al. (1989, supra). In order to confirm the presence of transformation vector DNA sequences within the transformed cells, Southern hybridization blots were prepared using DNA isolated from parental *N. gaditana* strain CCMP1894 cells and several putative algal transformants. Total genomic DNA, including both chloroplast and nuclear contents, is isolated using a Meta-G-Nome DNA Isolation Kit (Epicentre Biotechnologies, Madison, Wis.), as described in Example 1, and then further purified using either the DNeasy kit (Qiagen) or the Genomic DNA Clean & Concentrator™ Kit (Zymo Research Corp., Irvine, Calif.). Restriction digestion is typically performed on 1 µg of each total gDNA sample with restriction enzyme PshAI or SalI overnight. The digested DNA samples are then concentrated using a DNA Clean & Concentrator™-5 Kit (Zymo Research Corp., Irvine, Calif.) and loaded on a 1% agarose gel. As molecular weight marker, lambda DNA digested with HindIII and labeled with digoxigenin (DIG) (Roche; Cat#11218590910) is typically used. After electrophoresis, DNA from agarose gel was transferred to a nitrocellulose membrane using the iBlot® Gel Transfer Device (Invitrogen, Carlsbad, Calif.). The DNA was subsequently cross-linked to the membrane using a Stratalinker UV Crosslinker (Stratagene) with autocrosslink setting at 120 mJ. The membrane was then hybridized with a single-stranded DNA probe which is a 554 bp PCR product having nucleotide sequence corresponding to the 3' end of the SV40 promoter and the 5' half of the ble gene. The probe was pre-labeled with digoxigenin (DIG) using the Roche PCR DIG Probe Synthesis Kit (Roche, Cat#11636090910). Probe hybridization was detected using an alkaline phosphatase conjugated anti-DIG antibody (Roche; Cat#11093274910) and the ECF™ reagents (enzymatic chemifluorescence, GE Healthcare, Cat#RPN3685). Chemiluminescent signals of hybridizing probe are detected using the Typhoon™ FLA9000 (GE Healthcare).

Southern blot analysis confirmed that algal colonies obtained from the transformation of the vector constructs described in Example 2 were bone fide transformants as specific band(s) were detected with the probe for the ble selectable marker.

Quantitative RT-PCR (qRT-PCR)

In some instances, the relative strength of the promoters disclosed herein is also examined using quantitative RT-PCR techniques (qRT-PCR). qRT-PCR analyses are typically carried out using cell cultures that are in mid-log phase of growth. RNA preparation are performed with TRIzol® reagent (Life Technologies, Carlsbad, Calif.) by using the protocol recommended by the manufacturer, followed by a DNAse I treatment step (DNAse I, New England Biolabs, Ipswich, Mass.) and a spin-column based RNA clean-up step using RNA Clean-up Kit™ (Zymo Research). Typically, the gScript™ cDNA SuperMix (Quanta Biosciences, Gaithersburg, Md.) is used for the synthesis of cDNA, which is subsequently used as template for qPCR using the PerfeCTa® SYBR® Green FastMix® (Quanta Biosciences) using protocols recommended by the manufacturer. In general, the qPCR reactions are performed on a Bio-Rad CFX96 system. In these experiments, the expression level of TurboGFP reporter gene is typically normalized to the expression level of the ble selectable marker. As TurboGFP reporter and the ble marker are both in the same vector, they are expected to be present in the transformants at the same copy number and, as they are cloned adjacent to each other in the transformation vector, positional effects are expected to affect the expression of both genes in a similar manner.

Example 5

Examination and Evaluation of Promoter Activity

This Example describes experimental detail of the evaluation of several regulatory regions for promoter activity in a microalgal host, Nannochloropsis gaditana, using fluorescent microscopy techniques. Genetic transformation of Nannochloropsis was carried out using a procedure described in Example 3 above, where algal transformants were recovered by selection on Zeocin™ containing agar plates, and subsequently assayed by a colony-PCR technique for the presence of the selectable marker gene ble (as described in Example 4 above). Prior to transformation, recombinant vectors in which a TurboGFP reporter gene was placed under control of the regulatory regions being tested, were linearized by restriction enzyme digestion and the digested DNA was purified by phenol-chloroform extraction. For electroporation experiments, approximately 5-10 μg of the digested DNA was used. The cells were then incubated at room temperature under constant light (~50 μE/m²/s) for 4-5 weeks until algal colonies started to appear on agar plates. Transformants were assayed individually by colony PCR technique for the presence of the selectable marker gene ble. Liquid suspension cultures for each of the algal transformants were initiated as individual cell lines in liquid L1–Si+ 10×N&P media supplemented with 5 mg/L Zeocin™, followed by microscopy examination for green fluorescence expression. GFP fluorescence of transformed cells was examined using a Guava EasyCyte™ Plus flow cytometer (EMD Millipore, Billerica, Mass.) using the FL1 channel (excitation 488 nm, emission 530 nm). TABLE 3 summarizes data from an experiment in which green fluorescence was analyzed for multiple N. gaditana cell lines transformed with various N. gaditana promoters, each driving expression of the TurboGFP reporter gene. In this experiment, the relative fluorescence level for a transformed cell line was calculated as the mean fluorescence of the population of cells that exhibited fluorescence above background (~10 units). The vector pSGE05140 containing a N. gaditana eIF3 promoter was used as a positive control for comparison.

Fluorescence was undetectable in untransformed cells of N. gaditana CCMP1894 (i.e. negative control) while the positive control pSGE05140-2 exhibited fluorescence at ~329 units. Green fluorescence was also observed from cells transformed with six constructs pSGI-JU-33, pSGI-JU-34, pSGI-JU-35, pSGI-JU-36, pSGI-JU-37, and pSGI-JU-38. On average, all of the promoters tested in this experiment showed similar level of fluorescence. In particular, the ribosomal large subunit L4 promoter and the TCTP promoter produced individual transformants with significantly higher fluorescent signals. In fact, some transformants containing either the RP-L4 promoter or the TCTP promoter exhibited greater than 1000 units of fluorescence. In addition, the level of expression of TurboGFP based on fluorescence varied widely among cell lines containing the same construct; this expression variation could be due to positional effect and/or copy number of the vector insertions in the genome.

TABLE 3

Green fluorescence analyses of algal cell lines transformed with six regulatory regions isolated from Nannochloropsis gaditana.

| Construct Name | Promoter | No. of GFP + lines (out of 16 tested) | Fluorescence (units) | | |
|---|---|---|---|---|---|
| | | | average | lowest | highest |
| Untransformed | N/A | N/A | — | — | — |
| WT035-pSGE05140-2 | eIF3 | N/A | 323 | n/a | n/a |
| pSGI-JU-33 | RP-L13e | 11 | 299 | 135 | 750 |
| pSGI-JU-34 | RP-L4 | 15 | 398 | 154 | 1137 |
| pSGI-JU-35 | RP-L5 | 13 | 313 | 145 | 803 |
| pSGI-JU-36 | RP-S4e | 4 | 197 | 151 | 286 |
| pSGI-JU-37 | RP-S8e | 6 | 232 | 151 | 407 |
| pSGI-JU-38 | TCTP | 13 | 428 | 133 | 1065 |

A number of embodiments of the invention have been described. Nevertheless, it will be understood that elements of the embodiments described herein can be combined to make additional embodiments and various modifications may be made without departing from the spirit and scope of the invention. Accordingly, other embodiments, alternatives and equivalents are within the scope of the invention as described and claimed herein.

Headings within the application are solely for the convenience of the reader, and do not limit in any way the scope of the invention or its embodiments.

All publications and patent applications mentioned in this specification are herein incorporated by reference to the same extent as if each individual publication or patent application was specifically can individually indicated to be incorporated by reference. Throughout this disclosure, various information sources are referred to and are, where specifically noted, incorporated by reference. These information sources include, for example, World Wide Web browser-inactive page addresses. The reference to such information sources is solely for the purpose of providing an indication of the general state of the art at the time of filing. While the contents and teachings of each and every one of the information sources can be relied on and used by one of skill in the art to make and use embodiments of the invention, any discussion and comment in a specific information source should in no way be considered as an admission that such comment was widely accepted as the general opinion in the field.

What is claimed is:

1. An isolated nucleic acid molecule, comprising a nucleic acid sequence exhibiting 90% or greater sequence identity to a nucleic acid sequence selected from the group consisting of SEQ ID NO: 1 through SEQ ID NO: 16, operably linked a heterologous polynucleotide sequence encoding a protein of interest.

2. The nucleic acid molecule according to claim 1, wherein said nucleic acid sequence comprises a promoter.

3. The nucleic acid molecule according to claim 2, wherein said promoter comprises one or more cis-acting elements.

4. The nucleic acid molecule according to claim 1, wherein said nucleic acid molecule comprises a 5' untranslated sequence.

5. The nucleic acid molecule according to claim 1, wherein said heterologous polynucleotide is operably linked to a 3' untranslated region.

6. The nucleic acid molecule according to claim 1, wherein said nucleic acid molecule comprises an intron.

7. A nucleic acid construct comprising a nucleic acid molecule according to claim 1, wherein said nucleic acid sequence comprises a promoter.

8. The nucleic acid construct according to claim 7, wherein said heterologous polynucleotide sequence is operably linked to a 3' transcription termination polynucleotide sequence.

9. The nucleic acid construct according to claim 7, wherein said heterologous polynucleotide molecule encodes a gene involved in modulating the phenotype of a trait selected from the group consisting of carbohydrate content, cell wall components, enzyme production, growth and development, herbicide tolerance, isoprenoid content, modified amino acid content, modified biomass yield, modified fatty acid/oil content, modified oil production, nitrogen utilization, photosynthesis capacity, and production of pigments.

10. The nucleic acid construct according to claim 7, wherein said heterologous polynucleotide molecule encodes a gene involved in modulating herbicide tolerance.

11. The nucleic construct of claim 10, wherein said nucleic acid sequence encodes an enzymatic activity selected from the group consisting of acetyl coenzyme-A carboxylase (ACCase), aminoglycoside phosphotransferase, anthranilate synthase, bromoxynil resistant nitrilase, cytochrome P450-NADH-cytochrome P450 oxidoreductase, dalapon dehalogenase, glutathione reductase, glyphosate acetyl transferase, glyphosate oxidoreductase, glyphosate resistant EPSPS, hydroxyacetoacid synthase (AHAS), hydroxyphenyl pyruvate dehydrogenase (HPPD), isoprenyl pyrophosphate isomerase, lycopene cyclase, phosphinothricin acetyl transferase (PAT), phytoene desaturase, prenyl transferase, protoporphyrinogen oxidase, and superoxide dismutase (SOD).

12. An isolated transformed microbial or plant cell comprising a nucleic acid construct according to claim 1.

13. The isolated cell according to claim 12, wherein said cell is a microbial cell.

14. The isolated cell according to claim 13, wherein said microbial cell is a microalgal cell.

15. The isolated cell according to claim 12, wherein said cell is stably transformed with said nucleic acid construct.

16. A method of making a transformed cell, wherein said method comprises introducing into an isolated plant or microbial cell a nucleic acid molecule according to claim 1.

17. The method according to claim 16, wherein the transformed cell is a microalgal cell.

18. An isolated nucleic acid molecule, comprising a nucleic acid sequence that comprises at least 300 contiguous nucleotides consisting of any of SEQ ID NO: 1-16, operably linked to a heterologous polynucleotide sequence encoding a protein of interest.

19. The nucleic acid construct comprising a nucleic acid molecule according to claim 18, wherein said nucleic acid sequence comprises a promoter.

20. The nucleic acid construct according to claim 19 wherein said heterologous polynucleotide encodes a gene involved in modulating the phenotype of a trait selected from the group consisting of carbohydrate content, cell wall components, enzyme production, growth and development, herbicide tolerance, isoprenoid content, modified amino acid content, modified biomass yield, modified fatty acid/oil content, modified oil production, nitrogen utilization, photosynthesis capacity, and production of pigments.

21. An isolated transformed plant or microbial cell comprising a nucleic acid construct according to claim 19.

22. The isolated transformed cell according to claim 21, wherein said transgenic cell is a microbial cell.

23. The isolated transformed cell according to claim 22, wherein said microbial cell is a microalgal cell.

* * * * *

SEQUENCE LISTING

<160> NUMBER OF SEQ ID NOS: 32

<210> SEQ ID NO 1
<211> LENGTH: 1000
<212> TYPE: DNA
<213> ORGANISM: Nannochloropsis gaditana

```
<220> FEATURE:
<221> NAME/KEY: misc_feature
<223> OTHER INFORMATION: SGI Promoter ID NO. EMRE1EUKS708914
<220> FEATURE:
<221> NAME/KEY: misc_feature
<223> OTHER INFORMATION: SGI cDNA ID NO. EMRE1EUKS157014
<220> FEATURE:
<221> NAME/KEY: misc_feature
<223> OTHER INFORMATION: Translationally Controlled Tumor Protein (TCTP)
<220> FEATURE:
<221> NAME/KEY: misc_feature
<222> LOCATION: (954)..(1000)
<223> OTHER INFORMATION: 5' untranslated region

<400> SEQUENCE: 1
cgtgcaggtg tacagattga aggaaacaat ggagatatct ttggcagttg aaaaccgtgt      60
tcgaatcatg ctcttctact ctccaactga gacgaaattt atagcgccat gtcgcttctg     120
actaccaggc ttaggaaggc ctcatcacaa gctggatcgg ttcgaattaa gcaggcactg     180
aagccaagct tgcaagacag ccacctttta attctctcaa aacactttct caattcagcc     240
cggtaaatat gccgattcac agcggccaag atagagggga ggttagcaag aatgttgcga     300
tccctcccca gtcgttgcct cgcacacaac ctaggacttc acctttccat ggaaaattga     360
gaagtgaata ttggttttct tacggcatat cagatgaaat catgacccct aaacatgaag     420
agctgcaggc aaaacacctg ctctggacga gcacgatgaa atctcgagaa cccgccgtac     480
ttcagttgat cccgcatgat gacggccgcc attgaaataa gccacctcac tttattctag     540
caccgatttc caccgttgtg agggccgaac gaggacaatt tcgtgcgaaa caagcacgaa     600
cacgcacacg attagtagga cagacgagca gatcgatggc atgcggcacg gtctcgcgtt     660
ctcggcgacc aggacaacgg agcagaggga ggcctgccga gttccgaggg gcattttagt     720
cccaaaattg tgttgacacg tgaacaagtg gcttgaaaag aggaaggaaa tgcctgggtt     780
tcccttcgag agcgggaact cgcttgtgcg tcatcctagc tacccatggt cctttgtgg     840 gggaggctgt ttcgtcctac cgaatgtgtg gcgctccatg catcttctgc ctcccaaacc     900
accaacatga gcacgcgaag gaaggagaaa aaagtggccg caacgttctc ttctcatatt     960
tattgtctca tcacaaacat aggtacataa tacaacaatc                          1000

<210> SEQ ID NO 2
<211> LENGTH: 1000
<212> TYPE: DNA
<213> ORGANISM: Nannochloropsis gaditana
<220> FEATURE:
<221> NAME/KEY: misc_feature
<223> OTHER INFORMATION: SGI Promoter ID NO. EMRE1EUKS708913
<220> FEATURE:
<221> NAME/KEY: misc_feature
<223> OTHER INFORMATION: SGI cDNA ID NO. EMRE1EUKS155452
<220> FEATURE:
<221> NAME/KEY: misc_feature
<223> OTHER INFORMATION: Ribosomal Protein L13e
<220> FEATURE:
<221> NAME/KEY: misc_feature
<222> LOCATION: (983)..(1000)
<223> OTHER INFORMATION: 5' untranslated region

<400> SEQUENCE: 2
ttgaagaaag aaaaccctaa attgtccctt ctatcacacg taccgccaac ttccgcaccc      60
gtgactccaa agtttgtaca ttgttgttgt gagtggatga tggggtcgac ccgattgaag    120
acgagggttg actctccgat agggaataag acgggatatc aggaggcagc atggatgggg    180
ccctttcgcc tactgcgtgt ccgccggacg cactcgtgct gcctttgctt ttgctagact    240
```

| | |
|---|---|
| tttgcgccgg tgtccacatc tccagattta tgttattaag cctacgacca acaaaaatgg | 300 |
| cgttcgaagc caatcatcgt ataatcatcg agcttcgcac gtcctacaag gtaagaagga | 360 |
| ggggaggttg gtgctcctgc tgtagttgtc gcagcgacta gcagacgaat tttgaagaaa | 420 |
| ttactgactc aagctacgga gttaaaatac cccgcctacc tctgattcgc atcccaacat | 480 |
| agactagtga caagcagcgt caacctgcag tcgccataga actcgcaggc cgcactaaag | 540 |
| cgagggcggg gggcagggtc tggccccggt ccgcggggac agacatgtgt gcctcaaacc | 600 |
| ccccatcgcc atccactcct ttaccttcgg cctcccgggg cttgatctcg agtgcagggt | 660 |
| cgtgggtttc ttacgggaat aatgggatga tcatctgaga tgcttttttg ggggacagag | 720 |
| tgagacatag gacggaggaa ggagcgtcga ggggtagatg gacggctgga aaggctccag | 780 |
| actgtcctcc ccttcgttgt cttcttcttg ggcggagcgc ccacaatctt gtccttgtgg | 840 |
| ttcgtcaata ttcgcagacg tcgtcgtgag atttgtgcac tgctctggat gaacgtgcct | 900 |
| cgttttcaag gacgagactg caatggtcat taaaagagcg tggggagctc cacctcatga | 960 |
| cccttttttct cctccctccc ctccattccc ctaaggcagg | 1000 |

```
<210> SEQ ID NO 3
<211> LENGTH: 1000
<212> TYPE: DNA
<213> ORGANISM: Nannochloropsis gaditana
<220> FEATURE:
<221> NAME/KEY: misc_feature
<223> OTHER INFORMATION: SGI Promoter ID NO. EMRE1EUKS708905
<220> FEATURE:
<221> NAME/KEY: misc_feature
<223> OTHER INFORMATION: SGI cDNA ID NO. EMRE1EUKS154308
<220> FEATURE:
<221> NAME/KEY: misc_feature
<223> OTHER INFORMATION: Ribosomal Protein L4
<220> FEATURE:
<221> NAME/KEY: misc_feature
<222> LOCATION: (954)..(1000)
<223> OTHER INFORMATION: 5' untranslated region
```

<400> SEQUENCE: 3

| | |
|---|---|
| cgatgccagg gtcccccacca ctgcagccac gtgtcgggca cattccatgc gcagacggtc | 60 |
| gtacaaccgg gccccccattt tgtgtacgca taaatttttcc acggccctgt aaagttcctc | 120 |
| gtagctgata gctactgcag tcttgctttg caccgccacc actgcctgtc tcagaacctc | 180 |
| ccaggtcgca tcttcaaagt tttccggtag ctttggttgg actttaaacg gtcgaatcac | 240 |
| cattttctta ttcgatcccc ctgcggcccc attgttgccg cggttgttgc cttggacagt | 300 |
| cgcatttcgg ctggacatga ctaagcctgc cggccgcgat tgcgaggagg acgccgccgc | 360 |
| cgacatcccg cttgatgatt aatgcttcga gaagcgtctg aacgctacag aaaacaatct | 420 |
| acctagaatg taatcaatgg ggggaagtga ggtcggagaa gagctaagac aagaattatc | 480 |
| aggtcctcat tacgagaaag tctccgcagc caaatcttct tttgagtgct tctatggta | 540 |
| tcacagagca gcatatgtag agcgttccac aattgcctat caagttacgg ggtaggacgc | 600 |
| agtcctccat aagagcagca aggcctttct atgttgcgct tgcctccccg ttcctgctct | 660 |
| ccgcttcgat aggtctatgc gtccaagatt tacacaggtc tgtggcagcg atgacgccat | 720 |
| ccttgttcgt cgccccaatg gctctcaagc gcccttgacc ctcaatcctc ttggtgtgtg | 780 |
| caatgaacca acataagctt ttcgcagttt cttgtgtttg caagagatcc aattgggtaa | 840 |
| tgcgcgttta gtgacagtgt gaagtgccga gctgaggacc gtgatgaact tacgcagcc | 900 |
| actgatgctt ctatcgcctc ctactcgctt ctcttttgac ggacacacct tatttacacc | 960 |

```
tcgtttttaa aattagattt gtgcacatac gtacagcatt              1000
```

<210> SEQ ID NO 4
<211> LENGTH: 961
<212> TYPE: DNA
<213> ORGANISM: Nannochloropsis gaditana
<220> FEATURE:
<221> NAME/KEY: misc_feature
<223> OTHER INFORMATION: SGI Promoter ID NO. EMRE1EUKS708903
<220> FEATURE:
<221> NAME/KEY: misc_feature
<223> OTHER INFORMATION: SGI cDNA ID NO. EMRE1EUKS157216
<220> FEATURE:
<221> NAME/KEY: misc_feature
<223> OTHER INFORMATION: Ribosomal Protein L5
<220> FEATURE:
<221> NAME/KEY: misc_feature
<222> LOCATION: (917)..(961)
<223> OTHER INFORMATION: 5' untranslated region

<400> SEQUENCE: 4

```
gcagaaccag aacagaagat tcctcgatcc aatttctcgg gcctggaagg cggaagagga      60
cgtaactttc aacaagatag cgtcttggga agacaagttc tcgcaggggc aacctcctcg     120
attctaagag tctgtggaca aaagcataat cgtcagttgt tcgagcgtac tcattacgga     180
tcatcttcct tctgttcatg cagccatcgt gaaaccgcga tggacaggcg ataacatcac     240
ggaagaggaa gcaagctcgc ccagatgccg ctgatgagcg cttttccgag gaaaggaaaa     300
gagtgactag catgaacacg cagtgcgtta cccagggcaa gccaacaacc tgccagagca     360
ggcatcgtgc ccgaaggtct ggcgtccagc accacaagac acgtcctccc agcagtccat     420
ttggcatgtg ccggagtccg aactaaccta gagccccggg cgagggttta catcccacag     480
actgtgatag cttctcgccg cctgcgtcgc tctcggccct ccgtgggtgg tcgagggcga     540
gaagtgaagc accacgggcg tgtgcatggg ggcttggtac caggtaggga tggccacacg     600
tctttagtgt tggatggaag gccatgaccc tagtgtcaga aatggtggtt gttttgggtg     660
cttatttcgt ctgccagact tggtaaccaa ccattctcag cactgccgca gagaaggagg     720
gcggggggcga aagagggctt attttcttgg tgtctaccag gttctttact tgagtaggag     780
tcttgttttg gcatactgca tataaatgtg ccactgtgca tggaaggata aagggctat     840
ctcgcgtttg gatgcagtgc ctcgtacagc ctcgagaggc ttcgccttac gccgcgaccc     900
atgtttctac ttttctcgc aatcgcacag cctttatctc cgcagcacct ggctcgggac     960
g                                                                    961
```

<210> SEQ ID NO 5
<211> LENGTH: 444
<212> TYPE: DNA
<213> ORGANISM: Nannochloropsis gaditana
<220> FEATURE:
<221> NAME/KEY: misc_feature
<223> OTHER INFORMATION: SGI Promoter ID NO. EMRE1EUKS708920
<220> FEATURE:
<221> NAME/KEY: misc_feature
<223> OTHER INFORMATION: SGI cDNA ID NO. EMRE1EUKS154998
<220> FEATURE:
<221> NAME/KEY: misc_feature
<223> OTHER INFORMATION: Ribosomal Protein S4e
<220> FEATURE:
<221> NAME/KEY: misc_feature
<222> LOCATION: (358)..(444)
<223> OTHER INFORMATION: 5' untranslated region

<400> SEQUENCE: 5

```
tcgtcatcct tcctcctcat ctggacgcat atgagatctt ttacgtcatc ctctcttctc      60
```

```
atccccccct ccctcctccc ttcttatcac ccttcctttc caccggcttg ctccctacgt      120
tcactagtgg tgtggctgtg tctctggctt tgacttcttt gggccctgtg ttcgcacttg      180
ccactgcaag ttctggtttt ggcacgaaaa ataccttgtg tgtgaggatg agggttgcga      240
ttgatttctt tcgcgttgga cggaggcgct ctcatcacaa cgtctccctc cagccacaca      300
cgccctcttc gctgtctttc acctccatcc caccctctta attaacgcgt tcctaaacca      360
ttccttcgca taccacattc ttgacacacg taaaatttca cagtgcgcga tacttctgaa      420
ttggttgctc cgccgtaatc aatc                                            444
```

<210> SEQ ID NO 6
<211> LENGTH: 961
<212> TYPE: DNA
<213> ORGANISM: Nannochloropsis gaditana
<220> FEATURE:
<221> NAME/KEY: misc_feature
<223> OTHER INFORMATION: SGI Promoter ID NO. EMRE1EUKS708902
<220> FEATURE:
<221> NAME/KEY: misc_feature
<223> OTHER INFORMATION: SGI cDNA ID NO. EMRE1EUKS150213
<220> FEATURE:
<221> NAME/KEY: misc_feature
<223> OTHER INFORMATION: Ribosomal Protein S8e
<220> FEATURE:
<221> NAME/KEY: misc_feature
<222> LOCATION: (799)..(961)
<223> OTHER INFORMATION: 5' untranslated region

<400> SEQUENCE: 6

```
cttgctagca ttgttttcca aatagaagat gtagactgct tgcatcccca ttgggttaca       60
tggcttgcgt tgtaagcaga aaggaggcct aggcgatgat acgtgtcgag cacccaggcg      120
gttctacctt cgtcgtcgct acaatcatct accaggaaaa aatgtcccac gcccagcaga      180
tggtggtact ccaaccattc tgcaaggctt ctgggagtgt ttcgcacacg tgtcaaaata      240
catagcttgt gcggctggga ggagggtatg ctcgagttgg gcaaattagt taccgatgag      300
gcaagaagtg atgacatgga cggaggcgac acgaatgtag gaaagatgat tacaaagctt      360
aatactccaa ccaaagcgac aatggaagat gcggctaata tgtacaggca acgaccatga      420
ccacaaaagc tgcgaggaca cgtcaatttg ttggggagca ttggacctag gacacaaggc      480
atctcaggaa gcactttgca tctctgaaca atgcggcaaa tatacacgca tacctctcaa      540
ccacctggaa gaaagggtgc tgaaaatcgt gaatgcgacg tggcctgtcg atgggtgtat      600
agagaagatg gctttggtac gaatatatca atatgggccg agagtctgtt cccacccggg      660
gcgagtgagt ggtgagaaga aggctggcca tattttatgg cggatcacgg ttggcggtgc      720
tcgcgtgcgt ggcgctcgca ttttggcacg ataaacttct cacatgctgt ctcgtttgtc      780
cttgtatccc ttcctgtcgc cattctttac aggaaagagc attttaattg attggacgca      840
gaggaggcag aggatcacgt atccgaagaa gaggtcgaag gccgcctcca acttacacgc      900
gtggctgcta ctccacgcag gaactcatcg ttaggcagaa tcacacatac atttataaaa      960
c                                                                     961
```

<210> SEQ ID NO 7
<211> LENGTH: 300
<212> TYPE: DNA
<213> ORGANISM: Nannochloropsis gaditana
<220> FEATURE:
<221> NAME/KEY: misc_feature
<223> OTHER INFORMATION: SGI Promoter ID NO. EMRE1EUKG11871
<220> FEATURE:

```
<221> NAME/KEY: misc_feature
<223> OTHER INFORMATION: 50S ribosomal protein subunit L11

<400> SEQUENCE: 7
ttaaattgaa aagatacaag caaatattga aaaaaaaaat aataattaaa tgtgaatttt      60
catcaggaaa atgaatagcg tctttagttc agttggtaga acgtaggtct ccaaaaccta     120
atgtcgaggg ttcaagtcct tcaaggcgtg ttttatgtct aatataatat ctacttataa     180
taactgttta cactcaaaat attatttgat aatatcaagt taagaaaaat agttttttat     240
tcactaattc aaaataaaaa gcttgaattt tagaacaaac cattaaaact tgcgtaaaaa     300

<210> SEQ ID NO 8
<211> LENGTH: 201
<212> TYPE: DNA
<213> ORGANISM: Nannochloropsis gaditana
<220> FEATURE:
<221> NAME/KEY: misc_feature
<223> OTHER INFORMATION: SGI Promoter ID NO. EMRE1EUKG11849
<220> FEATURE:
<221> NAME/KEY: misc_feature
<223> OTHER INFORMATION: 50S ribosomal protein subunit L13

<400> SEQUENCE: 8
acacctctcg agttattaaa acgaattggt ttaaatgaaa acgagttaat cactatagaa      60
aaatctttga atttaattgg tttatctata aatcttgata aaaatttgaa atgggaattg     120
attccaagtt cattaccact ttaaaatttt gttaattact tacattgagc aaatataaaa     180
ttttaaaacc tatctaaaac a                                                201

<210> SEQ ID NO 9
<211> LENGTH: 200
<212> TYPE: DNA
<213> ORGANISM: Nannochloropsis gaditana
<220> FEATURE:
<221> NAME/KEY: misc_feature
<223> OTHER INFORMATION: SGI Promoter ID NO. EMRE1EUKG11833
<220> FEATURE:
<221> NAME/KEY: misc_feature
<223> OTHER INFORMATION: 50S ribosomal protein subunit L36

<400> SEQUENCE: 9
gggcttatgt tagcactgtt agtaggagtt tccgatatac ttgataatta ttatccaaca      60
atcggcttaa aatcaaattt aagctcttta cttattttat tcggaacaat gctcgattta     120
gaagatcgac tttttgattt aggactaaaa aaagcttaat ctgatatttt taaaatctat     180
atatacataa actattaaaa                                                  200

<210> SEQ ID NO 10
<211> LENGTH: 200
<212> TYPE: DNA
<213> ORGANISM: Nannochloropsis gaditana
<220> FEATURE:
<221> NAME/KEY: misc_feature
<223> OTHER INFORMATION: SGI Promoter ID NO. EMRE1EUKG11868
<220> FEATURE:
<221> NAME/KEY: misc_feature
<223> OTHER INFORMATION: 50S ribosomal protein subunit L16

<400> SEQUENCE: 10
ggtgcagaaa ttgcaaggac agaatgggta cgtgaaggaa gagtcccact tcatacatta      60
caagcaagat tagattacgc aactgagaga gcacaaacaa tatatggtat attaggtatc     120
aaaatttgga tgtgtaaagg ctaaagttta gttaaaaatt gtaactgaaa attttacgtt     180
```
ttaattacaa ataaaaaaat                                              200

<210> SEQ ID NO 11
<211> LENGTH: 200
<212> TYPE: DNA
<213> ORGANISM: Nannochloropsis gaditana
<220> FEATURE:
<221> NAME/KEY: misc_feature
<223> OTHER INFORMATION: SGI Promoter ID NO. EMRE1EUKG11888
<220> FEATURE:
<221> NAME/KEY: misc_feature
<223> OTHER INFORMATION: 30S ribosomal protein subunit S2

<400> SEQUENCE: 11
tgaaagattt caagaaaaaa aataatataa attattaatt tgaatgactt ctataaagat    60
taaaccaaat taaatgggta taattaaaaa gcaatatttt aaggattttc taaattatgt   120
ataatttata taatgtttaa aatattgtct tttatatatc aaacgacaat tacaaaatat   180
acaaaaacta atacaaaaat                                              200

<210> SEQ ID NO 12
<211> LENGTH: 200
<212> TYPE: DNA
<213> ORGANISM: Nannochloropsis gaditana
<220> FEATURE:
<221> NAME/KEY: misc_feature
<223> OTHER INFORMATION: SGI Promoter ID NO. MRE1EUKG11818
<220> FEATURE:
<221> NAME/KEY: misc_feature
<223> OTHER INFORMATION: 50S ribosomal protein subunit L34

<400> SEQUENCE: 12
gaatatagta gattatgtag tcaagagttt tcagaactta taaagagac acaatcacta     60 ataataaaca gtcttataaa ttttaatgaa ttaaataaaa cctatcttgg tgtttaattt   120
tatgttaaaa ttaaaaaaac tttaagtcaa agtaattatt tatttatttg acattactat   180
taaaataaag caggcctatt                                              200

<210> SEQ ID NO 13
<211> LENGTH: 200
<212> TYPE: DNA
<213> ORGANISM: Nannochloropsis gaditana
<220> FEATURE:
<221> NAME/KEY: misc_feature
<223> OTHER INFORMATION: SGI Promoter ID NO. EMRE1EUKG11812
<220> FEATURE:
<221> NAME/KEY: misc_feature
<223> OTHER INFORMATION: DNA-directed RNA polymerase subunit beta

<400> SEQUENCE: 13
tttgagaaaa gcagcaagac aaaaatcgcg tattagcaat gtactaaaaa aagttggtaa    60
accttaacct taaaatgaaa ttacataatt ttttttaatt tttaaagtaa tagatttatt   120
actttaaaag catacaacta gtttaaagct agttgtatgt atattttttg aaatgaataa   180
tcaaggagta aataaaataa                                              200

<210> SEQ ID NO 14
<211> LENGTH: 502
<212> TYPE: DNA
<213> ORGANISM: Nannochloropsis gaditana
<220> FEATURE:
<221> NAME/KEY: misc_feature
<223> OTHER INFORMATION: acetohydroxyacid synthase promoter

<400> SEQUENCE: 14

```
agagtggctc caacatatc cttttgcaag ccctaagatt ttttttctag attttctagc    60
tatatttcct cttttaacac gtatcatttt attttatctc attttaattg ttaaagaact   120 ttttactgt taattttca gtattccta cagtaatagt agaacaaagc cttcttttc      180 tagaagaaga ttttttttgt aataaatggc ctttaaaggc ttttttttcta atgaaatttt   240 tatttgccgt ttgtttatat cttttaccg ctgatttct tgtttagat ttattcataa    300 aataactctt cgattgttc gtaaaatagt ataaaatatt gtacaattaa aagagataaa   360
aaacaagcaa ttcttaacta aacgtattaa gtttgattaa cttcttaaat gttttaatttt  420 ttaataaaaa taattaatc aaagttttgt atttttttaag cagatcaaaa tttaattttta  480 aaaaattgaa aaaggtgaat aa                                            502
```

```
<210> SEQ ID NO 15
<211> LENGTH: 482
<212> TYPE: DNA
<213> ORGANISM: Nannochloropsis salina
<220> FEATURE:
<221> NAME/KEY: misc_feature
<223> OTHER INFORMATION: acetohydroxyacid synthase promoter

<400> SEQUENCE: 15
```

```
cttttgcaag ccctaagact tttttttctag attttctagc tatatttcct cttctaacac    60
gtatcatttt actttatctc attttaattg ttaaagaact ttttactgt taattttca    120 gtatttccta cagtaatagt agaacaaagt cttcttttc tagaagaaga tttttttgt    180 aataaatggc ctttaaaggc ttttttttcta atgaaatttt tatttgctgt ttgtttatat    240 cttttaccg ccgatttct tgtttagat ttattcataa aataactctt cgatttgttc    300
gtaaaatagt ataaaatact atacaattaa aagagataaa aaacaagcaa ttcttgacta    360
aacgtattaa gtttgattaa cttcttaaat gttttaattt ttaataaaaa taaattaatc    420
aaagttttgt atttttttaag cagatcaaaa tttaattttta aaaaattgaa aaaggtgaat   480
aa                                                                   482
```

```
<210> SEQ ID NO 16
<211> LENGTH: 238
<212> TYPE: DNA
<213> ORGANISM: Nannochloropsis oculata
<220> FEATURE:
<221> NAME/KEY: misc_feature
<223> OTHER INFORMATION: acetohydroxyacid synthase promoter

<400> SEQUENCE: 16
```

```
ctgatttct tgtttagat ttattcataa aataactctt cgatttgttc ctaaaatagt      60
ataaaatact atacaattaa aagagataaa aaacaagtaa ttcttaactg cttatgttaa   120
gtttaattaa cttttaaagt attttaatttt ttagtaaaaa taaataaatc aaaatttat   180 gttttttgaa atagcaattc aaaatttaat tttataaaaa agttgaaaag gtaaataa     238
```

```
<210> SEQ ID NO 17
<211> LENGTH: 43
<212> TYPE: DNA
<213> ORGANISM: Artificial sequence
<220> FEATURE:
<223> OTHER INFORMATION: Primer oSGI-JU-91

<400> SEQUENCE: 17
```

```
aggtataggg cggcgccttg aagaaagaaa accctaaatt gtc                      43
```

```
<210> SEQ ID NO 18
<211> LENGTH: 35
<212> TYPE: DNA
<213> ORGANISM: Artificial sequence
<220> FEATURE:
<223> OTHER INFORMATION: Primer oSGI-JU-92

<400> SEQUENCE: 18
ctcgtcgctc tccatcctgc cttaggggaa tggag                              35

<210> SEQ ID NO 19
<211> LENGTH: 38
<212> TYPE: DNA
<213> ORGANISM: Artificial sequence
<220> FEATURE:
<223> OTHER INFORMATION: Primer oSGI-JU-93

<400> SEQUENCE: 19
aggtataggg cggcgcccga tgccagggtc cccaccac                           38

<210> SEQ ID NO 20
<211> LENGTH: 35
<212> TYPE: DNA
<213> ORGANISM: Artificial sequence
<220> FEATURE:
<223> OTHER INFORMATION: Primer oSGI-JU-94

<400> SEQUENCE: 20
ctcgtcgctc tccataatgc tgtacgtatg tgcac                              35

<210> SEQ ID NO 21
<211> LENGTH: 39
<212> TYPE: DNA
<213> ORGANISM: Artificial sequence
<220> FEATURE:
<223> OTHER INFORMATION: Primer oSGI-JU-95

<400> SEQUENCE: 21
aggtataggg cggcgccgca gaaccagaac agaagattc                          39

<210> SEQ ID NO 22
<211> LENGTH: 35
<212> TYPE: DNA
<213> ORGANISM: Artificial sequence
<220> FEATURE:
<223> OTHER INFORMATION: Primer oSGI-JU-96

<400> SEQUENCE: 22
ctcgtcgctc tccatcgtcc cgagccaggt gctgc                              35

<210> SEQ ID NO 23
<211> LENGTH: 40
<212> TYPE: DNA
<213> ORGANISM: Artificial sequence
<220> FEATURE:
<223> OTHER INFORMATION: Primer oSGI-JU-97

<400> SEQUENCE: 23
aggtataggg cggcgcctcg tcatccttcc tcctcatctg                         40

<210> SEQ ID NO 24
<211> LENGTH: 36
<212> TYPE: DNA
<213> ORGANISM: Artificial sequence
<220> FEATURE:
<223> OTHER INFORMATION: Primer oSGI-JU-98
```

<400> SEQUENCE: 24
ctcgtcgctc tccatgattg attacggcgg agcaac                                36

<210> SEQ ID NO 25
<211> LENGTH: 42
<212> TYPE: DNA
<213> ORGANISM: Artificial sequence
<220> FEATURE:
<223> OTHER INFORMATION: Primer oSGI-JU-99

<400> SEQUENCE: 25
aggtataggg cggcgcccTt gctagcattg ttttccaaat ag                         42

<210> SEQ ID NO 26
<211> LENGTH: 41
<212> TYPE: DNA
<213> ORGANISM: Artificial sequence
<220> FEATURE:
<223> OTHER INFORMATION: Primer oSGI-JU-100

<400> SEQUENCE: 26
ctcgtcgctc tccatgtttt ataaatgtat gtgtgattct g                          41

<210> SEQ ID NO 27
<211> LENGTH: 24
<212> TYPE: DNA
<213> ORGANISM: Artificial sequence
<220> FEATURE:
<223> OTHER INFORMATION: Primer oSGI-JU-104

<400> SEQUENCE: 27
atggagagcg acgagagcgg cctg                                             24

<210> SEQ ID NO 28
<211> LENGTH: 25
<212> TYPE: DNA
<213> ORGANISM: Artificial sequence
<220> FEATURE:
<223> OTHER INFORMATION: Primer oSGI-JU-105

<400> SEQUENCE: 28
ctgaaggtca gggcgccttt ggtgc                                            25

<210> SEQ ID NO 29
<211> LENGTH: 39
<212> TYPE: DNA
<213> ORGANISM: Artificial sequence
<220> FEATURE:
<223> OTHER INFORMATION: Primer oSGI-JU-106

<400> SEQUENCE: 29
aggtataggg cggcgcccgt gcaggtgtac agattgaag                             39

<210> SEQ ID NO 30
<211> LENGTH: 38
<212> TYPE: DNA
<213> ORGANISM: Artificial sequence
<220> FEATURE:
<223> OTHER INFORMATION: Primer oSGI-JU-107

<400> SEQUENCE: 30
ctcgtcgctc tccatgattg ttgtattatg tacctatg                              38

<210> SEQ ID NO 31
<211> LENGTH: 20

```
<212> TYPE: DNA
<213> ORGANISM: Artificial sequence
<220> FEATURE:
<223> OTHER INFORMATION: Primer oSGI-JU-144

<400> SEQUENCE: 31
cctctgagct attccagaag                                              20

<210> SEQ ID NO 32
<211> LENGTH: 20
<212> TYPE: DNA
<213> ORGANISM: Artificial sequence
<220> FEATURE:
<223> OTHER INFORMATION: Primer oSGI-JU-145

<400> SEQUENCE: 32
aagttcgtgg acacgacctc                                              20
```